United States Patent
Ting

(10) Patent No.: US 7,172,877 B2
(45) Date of Patent: Feb. 6, 2007

(54) METHODS AND COMPOSITIONS FOR PEPTIDE AND PROTEIN LABELING

(75) Inventor: Alice Y. Ting, Allston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/754,911

(22) Filed: Jan. 9, 2004

(65) Prior Publication Data

US 2004/0209317 A1    Oct. 21, 2004

Related U.S. Application Data

(60) Provisional application No. 60/438,939, filed on Jan. 9, 2003.

(51) Int. Cl.
*C12Q 1/25* (2006.01)
*C40B 30/04* (2006.01)

(52) U.S. Cl. .................. 435/7.72; 435/7.6; 435/7.5; 435/7.1; 435/21.2; 530/350

(58) Field of Classification Search .......... 435/7.4, 435/7.72, 7.6, 7.5, 7.1, 21.2; 530/350
See application file for complete search history.

(56) References Cited

U.S. PATENT DOCUMENTS

| 5,168,057 A * | 12/1992 | Oh et al. ............... 435/174 |
| 5,723,584 A | 3/1998 | Schatz |
| 5,874,239 A | 2/1999 | Schatz |
| 5,932,433 A | 8/1999 | Schatz |
| 5,952,185 A * | 9/1999 | Huber et al. ............. 435/7.5 |
| 6,265,552 B1 | 7/2001 | Schatz |

OTHER PUBLICATIONS

Rhee et al, Protein Science, 13, 3043-50, (2004).*
Kwon et al, Protein Science, 2000, 9, 1530-39.*
Kwon et al, Protein Science, 2002, 11, 558-570.*
Kwon et al, Jrnl. Mol. Biol. 200, 304, 821-833.*
Chen et al., "Site-specific labeling of cell surface proteins with biophysical probes using biotin ligase," *Nature Methods*, Feb. 2005, pp. 99-104, vol. 2, No. 2.
Beckett et al., "A minimal peptide substrate in biotin holoenzyme synthetase-catalyzed biotinylation", *Protein Sci.*, 8(4): 921-929, 1999. Abstract Only.
Chapman-Smith et al., "Molecular biology of biotin attachment to proteins", *J. Nutr.*, 129: 477S-484S, 1999.
Cornish et al., "Site-specific protein modification using a ketone handle", *J. Am. Chem. Soc.*, 118: 8150-8151, 1996.
De Boer et al., "Efficient biotinylation and single-step purification of tagged transcription factors in mammalian cells and transgenic mice", *PNAS*, 100(13): 7480-7485, 2003.
Gaietta et al., "Multicolor and electron microscopic imaging of connexin trafficking", *Science*, 296: 503-507, 2002.
GENBANK Submission; NIH/NCBI; Accession No. M10123; Apr. 26, 1993 (last submission).

(Continued)

*Primary Examiner*—T. D. Wessendorf
(74) *Attorney, Agent, or Firm*—Wolf, Greenfield & Sacks, P.C.

(57) ABSTRACT

The invention provides compositions and methods of use thereof for labeling peptide and proteins in vitro or in vivo. The methods described herein employ biotin ligase mutants and biotin analogs recognized by such mutants.

22 Claims, 8 Drawing Sheets

OTHER PUBLICATIONS

Giriat et al., "Protein semi-synthesis in living cells", *J. Am. Chem. Soc.*, 125: 7180-7181, 2003.

Griffin et al., "Specific covalent labeling of recombinant protein molecules inside live cells", *Science*, 281: 269-272, 1998.

Heinis et al., "Selection of catalytically active biotin ligase and trypsin mutants by phage display", *Protein Engineering*, 14(12): 1043-1052, 2001.

Irie et al., "A digital fluorescent molecular photoswitch", *Nature*, 420: 759-760, 2002.

Keppler et al., "A general method for the covalent labeling of fusion proteins with small molecules *in vivo*", *Nature Biotechnology*, 21: 86-89, 2003.

Kiick et al., "Incorporation of azides into recombinant proteins for chemoselective modification by the Staudinger ligation", *PNAS*, 99(1): 19-24, 2002.

Link et al., "Cell surface labeling of *Escherichia coli* via copper(I)-catalyzed [3+2] cycloaddition", *J. Am. Chem. Soc.*, 125: 11164-11165, 2003.

Looger et al., "Computational design of receptor and sensor proteins with novel functions", *Nature*, 423: 185-190, 2003.

Mahal et al., "Engineering chemical reactivity on cell surfaces through oligosaccharide biosynthesis", *Science*, 276: 1125-1128, 1997.

Quellhorst et al., "Modification of Rab5 with a photoactivatable analog of geranylgeranyl diphosphate", *J. Biol. Chem.*, 276(44): 40727-40733, 2001.

Sato et al., "Site-specific modification of interleukin-2 by the combined use of genetic engineering techniques and transglutaminase", *Biochemistry*, 35: 13072-13080, 1996.

Saxon et al., "Cell surface engineering by a modified Staudinger reaction", *Science*, 287: 2007-2010, 2000.

Schatz et al., "Use of peptide libraries to map the substrate specificity of a peptide-modifying enzyme: a 13 residue consensus peptide specifies biotinylation in *Escherichia coli*", *Biotechnology*, 11(10): 1138-1143, 1993. Abstract Only.

Van Delden et al., "A chiroptical molecular switch with distinct chiral and photochromic entities and its application in optical switching of a cholesteric liquid crystal", *Chem. Eur. J.*, 10: 61-70, 2004.

Van Delden et al., "Photochemical and thermal isomerization processes of a chiral auxiliary based donor—acceptor substituted chiroptical molecular switch: convergent synthesis, improved resolution and switching properties", *Chem. Eur. J.*, 9: 2845-2853, 2003.

Wang et al., "Bioconjugation by copper (I)-catalyzed azide-alkyne [3+2] cycloaddition", *J. Am. Chem. Soc.*, 125: 3192-3193, 2003.

Weaver et al., "Corepressor-induced organization and assembly of the biotin repressor: A model for allosteric activation of a transcriptional regulator", *PNAS*, 98(11): 6045-6050, 2001.

Wilson et al., "*Escherichia coli* biotin holoenzyme synthetase / bio repressor crystal structure delineates the biotin- and DNA-binding domains", *Proc. Natl. Acad. Sci. USA*, 89: 9257-9261, 1992.

Yeo et al., "Cell-permeable small molecule probes for site-specific labeling of proteins", *Chem. Commun.*, 2870-2871, 2003.

Zhang et al., "A water-soluble azobenzene cross-linker for photocontrol of peptide conformation", *Bioconjugate Chemistry*, 14: 824-829, 2003.

Zhang et al., "A new strategy for the site-specific modification of proteins *in vivo*", *Biochemistry*, 42: 6735-6746, 2003.

\* cited by examiner

```
atgaaggataacaccgtgccactgaaattgattgccctgttagcgaacggtgaatttcac
 M   K   D   N   T   V   P   L   K   L   I   A   L   L   A   N   G   E   F   H
tctggcgagcagttgggtgaaacgctgggaatgagccgggcggctattaataaacacatt
 S   G   E   Q   L   G   E   T   L   G   M   S   R   A   A   I   N   K   H   I
cagacactgcgtgactggggcgttgatgtctttaccgttccgggtaaaggatacagcctg
 Q   T   L   R   D   W   G   V   D   V   F   T   V   P   G   K   G   Y   S   L
cctgagccatccagttacttaatgctaaacagatattgggtcagctggatggcggtagt
 P   E   P   I   Q   L   L   N   A   K   Q   I   L   G   Q   L   D   G   G   S
gtagccgtgctgccagtgattgactccacgaatcagtaccttcttgatcgtatcggagag
 V   A   V   L   P   V   I   D   S   T   N   Q   Y   L   L   D   R   I   G   E
cttaaatcgggcgatgcttgcattgcagaataccagcaggctggccgtggtcgccggggt
 L   K   S   G   D   A   C   I   A   E   Y   Q   Q   A   G   R   G   R   R   G
cggaaatggttttcgccttttggcgcaaacttatatttgtcgatgttctggcgtctggaa
 R   K   W   F   S   P   F   G   A   N   L   Y   L   S   M   F   W   R   L   E
caaggcccggcggcggcgattggtttaagtctggttatcggtatcgtgatggcggaagta
 Q   G   P   A   A   A   I   G   L   S   L   V   I   G   I   V   M   A   E   V
ttacgcaagctgggtgcagataaagttcgtgttaaatggcctaatgacctctatctgcag
 L   R   K   L   G   A   D   K   V   R   V   K   W   P   N   D   L   Y   L   Q
gatcgcaagctggcaggcattctggtggagctgactggcaaaactggcgatgcggcgcaa
 D   R   K   L   A   G   I   L   V   E   L   T   G   K   T   G   D   A   A   Q
atagtcattggagccgggatcaacatggcaatgcgccgtgttgaagagagtgtcgttaat
 I   V   I   G   A   G   I   N   M   A   M   R   R   V   E   E   S   V   V   N
caggggtggatcacgctgcaggaagcggggatcaatctcgatcgtaatacgttggcggcc
 Q   G   W   I   T   L   Q   E   A   G   I   N   L   D   R   N   T   L   A   A
atgctaatacgtgaattacgtgctgcgttggaactcttcgaacaagaaggattggcacct
 M   L   I   R   E   L   R   A   A   L   E   L   F   E   Q   E   G   L   A   P
tatctgtcgcgctgggaaaagctggataatttattaatcgcccagtgaaacttatcatt
 Y   L   S   R   W   E   K   L   D   N   F   I   N   R   P   V   K   L   I   I
ggtgataaagaaatatttggcatttcacgcggaatagacaaacagggggctttattactt
 G   D   K   E   I   F   G   I   S   R   G   I   D   K   Q   G   A   L   L   L
gagcaggatggaataataaaaccctggatgggcggtgaaatatccctgcgtagtgcagaa
 E   Q   D   G   I   I   K   P   W   M   G   G   E   I   S   L   R   S   A   E
aaataa
 K   -
```

METHODS AND COMPOSITIONS FOR PEPTIDE AND PROTEIN LABELING

RELATED APPLICATIONS

This application claims priority under 35 U.S.C. 119(e) to U.S. Provisional Patent Application No. 60/438,939, filed Jan. 9, 2003, entitled "SITE-SPECIFIC LABELING OF RECOMBINANT PROTEINS IN LIVING CELLS WITH ENGINEERED FLUOROPHORE TRANSFERASE", the entire contents of which are incorporated herein by reference.

GOVERNMENT SUPPORT

This invention was made in part with government support under grant number K22-HG002671-01 from the National Institutes of Health. The Government may retain certain rights in the invention.

BACKGROUND OF THE INVENTION

To track protein expression, localization, or conformational changes as components of cellular signaling pathways, biologists need general tools for the in vivo site-specific labeling of proteins with fluorophores or other useful probes. Traditional chemical methods rely on the nucleophilicity of cysteine or lysine side chains and are too promiscuous for in vivo use, and genetic methods such as fusion to green fluorescent protein (GFP) carry bulky payloads (GFP is 238 amino acids) and are limited in the color range and nature of the spectroscopic readout.

A survey of the existing methods for targeting small molecules to protein sequences reveals that the shorter the target sequence, the less specific the conjugation chemistry. For instance, very specific conjugation can be achieved by fusing the protein $O^6$-alkylguanine-DNA alkyltransferase (AGT) to the target protein of interest, and then adding a fluorescently-labeled $O^6$-benzylguanine suicide substrate for the AGT. (Keppler, A. et al. *Nat. Biotechnol.* 21, 86–89, 2003). However, the AGT tag is 207 amino acids and introduces a large amount of steric bulk. Smaller peptide tags are more desirable, but difficult to target with small molecules with high specificity. For example, cysteine labeling is not at all specific inside cells, and tetracysteine labeling (Griffin, B A et al. *Science* 281, 269–272, 1998), while much better, is still insufficiently specific for most applications and allows only a small set of probes to be introduced. Transglutaminase is already used to label glutamine side chains with fluorophores in vitro (Sato, H. et al. *Biochemistry* 35, 13072–13080, 1996), however it is relatively promiscuous for peptide and protein substrates, precluding its use in mammalian cells. In vitro labeling and microinjection has the disadvantage that protein localization and abundance may be altered. Polyhistidine tag methodology has the disadvantage that nickel is toxic, promiscuous, membrane impermeant and a quencher of fluorescence.

Accordingly, there exists a need for a method to label proteins and peptides that is specific and which offers a variety of a labeling options.

SUMMARY OF THE INVENTION

The invention relates in part to labeling of proteins (or fragments thereof) using biotin ligase mutants. The methods and compositions provided by the invention provide labeling specificity while also expanding the scope of compatible probe structures for labeling of proteins. Labeling of peptides or proteins can be performed in vitro or in vivo. The invention also provides, inter alia, biotin ligase mutants and biotin analogs and methods of use thereof for labeling proteins. It also provides screening methods for identifying further biotin ligase mutants and biotin analogs.

Thus, in one aspect, the invention provides a method for labeling a target protein comprising contacting a fusion protein with a biotin analog, and allowing sufficient time for the biotin analog to be conjugated to the fusion protein via an acceptor peptide, in the presence of a biotin ligase mutant, wherein the fusion protein is a fusion of the target protein and the acceptor peptide.

Various embodiments apply equally to this and other aspects of the invention. These are discussed below.

In one embodiment, the biotin analog may comprise an aliphatic carboxylic acid tail. In another embodiment and potentially additionally, the biotin analog may comprise an amino acid substitution at a trans-ureido nitrogen (N) of biotin. Examples of biotin analogs include but are not limited to N-ketone biotin analog, a ketone biotin analog, an N-azide biotin analog, an azide biotin analog, an N-acyl azide biotin analog, an NBD-GABA biotin analog, a 1,2-diamine biotin analog, an N-alkyne biotin analog and a tetrathiol biotin analog. The biotin analog may be fluorogenic. Alternatively, the biotin analog may be directly detectable. Examples include but are not limited to coumarin, fluorescein, rhodamine, rosamine, an Alexa™ dye, resorufin, oregon green, tetramethyl rhodamine, Texas Red® and BODIPY. In still other embodiments, the biotin analog is labeled with a directly detectable label, such as but not limited to fluorophore, a radioisotope, a contrast agent, an MRI contrast agent, a PET label, a phosphorescent label and a luminescent label. Alternatively, the biotin analog is labeled with an indirectly detectable label such as but not limited to an enzyme, an enzyme substrate, an antibody, an antibody fragment, an antigen, a hapten, a ligand, an affinity molecule, a chromogenic substrate, a protein, a peptide, a nucleic acid, a carbohydrate and a lipid. In still a further embodiment, the biotin analog is labeled with a membrane impermeant label.

The biotin analog may be labeled before or after conjugation to the fusion protein. In one embodiment, the acceptor peptide is fused to the target protein via a cleavable bond or linker.

The biotin analog may be labeled with a variety of labels, described herein. For example, the biotin analog may be labeled with a singlet oxygen radical generator such as but not limited to resorufin, malachite green, fluorescein or diaminobenzidine. The biotin analog may be labeled with an analyte-binding group, such as a metal chelator, non-limiting examples of which include EDTA, EGTA, a pyridinium, an imidazole and a thiol. The biotin analog may be labeled with a heavy atom carrier, such as but not limited to iodine. The biotin analog may be labeled with an affinity tag such as but not limited to a histidine tag, a GST tag, a FLAG tag and an HA tag. The biotin analog may be labeled with a photoactivatable cross-linker such as but not limited to benzophenones and aziridines. The biotin analog may be labeled with a photoswitch label such as but not limited to azobenzene. The biotin analog may be labeled with a photolabile protecting group such as but not limited to a nitrobenzyl group, a dimethoxy nitrobenzyl group or NVOC. The biotin analog may be labeled with a peptide comprising non-naturally occurring amino acids, examples of which are provided herein.

The target protein may be a cell surface protein, or an intracellular protein but it is not so limited. In one embodiment, the fusion protein is in a cell. Depending upon the method, the biotin ligase mutant may be expressed by a cell (for example the cell harboring the fusion protein) or it may be added to a protein in a cell free environment. In one embodiment, the cell is a eukaryotic cell while in another it is a bacterial cell. Examples of eukaryotic cell include but are not limited to a mammalian cell, a Drosophila cell, a Zebrafish cell, a Xenopus cell, a yeast cell or a C. elegans cell.

In one embodiment, the acceptor peptide comprises an amino acid sequence of SEQ ID NO: 4. In another embodiment, the acceptor peptide comprises an amino acid sequence of SEQ ID NO: 5. The acceptor peptide may be N- or C-terminally fused to the target protein.

In still another embodiment, the biotin ligase mutant has an amino acid substitution at 83, 89, 90, 91, 92, 107, 112, 115, 116, 117, 118, 123, 132, 134, 142, 186, 188, 189, 190, 204, 206, 207 or 235. In some embodiments, the amino acid substitution is at T90, C107, Q112, G115, Y132, S134, V189 or I207. In some important embodiments, the amino acid substitution is at T90 and includes but is not limited to T90G, T90A and T90V. In a particular embodiment, the amino acid substitution is at T90G and optionally the biotin analog is N-ketone biotin analog. The biotin ligase mutant may further comprise an amino acid substitution at N91 such as but not limited to N91S, N91G, N91A or N91L. In a particular embodiment, the biotin ligase mutant comprises amino acid substitutions of T90G and N91S. In a related embodiment, the biotin analog is N-alkyne biotin analog. In still other embodiments, the biotin ligase mutant comprises amino acid substitutions of T90G/N91G, T90A/N90A or T90A/N91L. In still other embodiments, the amino acid substitution is C107G, Q112M, G115A, Y132G, Y132A, S134G, V189G or I207S. The biotin ligase mutant may have an amino acid sequence of SEQ ID NO: 6 or SEQ ID NO: 7.

The method may be performed in a cell free environment or it may be performed in the context of a cell (e.g., in a cell or on a cell). The method may also be performed in a subject.

In another aspect, the invention provides a composition comprising a biotin ligase mutant that binds to a biotin analog. In one embodiment, the biotin ligase mutant comprises an amino acid substitution in a biotin interaction and activation domain. All of the foregoing embodiments relating to biotin ligase mutants and biotin analogs also apply to this aspect of the invention and thus will not be recited again. In another embodiment, the biotin ligase mutant is isolated. The biotin ligase mutant may have reduced binding affinity to biotin. In another embodiment, the biotin ligase mutant has wild type binding affinity to biotin.

In still another aspect, the invention provides a composition comprising a nucleic acid encoding a biotin ligase mutant comprising an amino acid substitution at 83, 89, 90, 91, 92, 107, 112, 115, 116, 117, 118, 123, 132, 134, 142, 186, 188, 189, 190, 204, 206, 207 or 235. As used herein, the amino acid positions recited herein are relative to the wild type biotin ligase having an amino acid sequence as shown in SEQ ID NO:2. It is to be understood that the biotin ligase mutant may comprise one or more of the aforementioned amino acid substitutions. In particular embodiments, the amino acid substitution is selected from the group consisting of T90G, T91A, T90V, N91S, N91G, N91A, N91L, C 107G, Q112M, Q112G, G115A, Y132G, Y132A, S134G, V189G and I207S. The nucleic acid is preferably isolated, but it is not so limited. In some embodiments, the nucleic acid is inducibly expressed. The nucleic acid may encode any of the biotin ligase mutants described herein. The invention further provides vectors that comprise nucleic acid that encode any of the biotin ligase mutants described herein and host cells that comprise these vectors. The invention further provides a process for preparing a biotin ligase mutant comprising culturing the host cells described herein and recovering the biotin ligase mutant from the culture.

In yet another aspect, the invention provides a composition comprising a biotin analog that binds to a biotin ligase mutant, wherein the biotin analog is alkyated at a trans-ureido nitrogen (N) of biotin. Examples of such biotin analogs include but are not limited to an N-ketone biotin analog, an N-azide biotin analog, an N-acyl azide biotin analog, and an N-alkyne biotin analog. In one embodiment, the biotin analog is not recognized by wild type biotin ligase. In another embodiment, the biotin analog is isolated. Other embodiments relating to biotin analogs and biotin ligase mutants are recited herein.

In another aspect, the invention provides a composition comprising a biotin analog that binds to a biotin ligase mutant, wherein the biotin analog is ketone biotin analog or NBD-GABA.

In still another aspect, the invention provides a phage display library comprising a biotin ligase mutant having an amino acid substitution at 83, 89, 90, 91, 92, 107, 112, 115, 116, 117, 118, 123, 132, 134, 142, 186, 188, 189, 190, 204, 206, 207 or 235. In one embodiment, the amino acid substitution is at T90, G115, Y132, C107, Q112, V189, I207 or S134. In another embodiment, the amino acid substitution is at T90 and may be but is not limited to T90G, T90A or T90V. In another embodiment, the biotin ligase mutant further comprises an amino acid substitution at N91 such as but not limited to N91S, N91G, N91A or N91L. In one embodiment, the biotin ligase mutant comprises amino acid substitutions of T90G and N91S. In another embodiment, it comprises one or more of the amino acid substitutions of C107G, Q112M, G115A, Y132G, Y132A, V189G, S134G, I207S, T90G/N91G, T90A/N91A and T90A/N91L. The amino acid substitution may be at 90, 91, 112, 115, 116, 132 or 188. In a particular embodiment, the library has at least about 1×10$^8$ or about 1×10$^9$ members.

In still another aspect, the invention provides a method for identifying a biotin ligase mutant having specificity for a biotin analog comprising contacting a biotin analog with an acceptor peptide in the presence of a candidate biotin ligase mutant molecule, and detecting a biotin analog that is bound to the acceptor peptide, wherein the presence of the biotin analog bound to the acceptor peptide indicates that the candidate biotin ligase mutant molecule is a biotin ligase mutant having specificity for the biotin analog. The candidate molecule may be a library member such as but not limited to a phage display library member. In one embodiment, the candidate molecule is bound to a solid support while in another it is soluble. Various embodiments of biotin analog are possible as recited herein. In one embodiment, detecting a biotin analog comprises detecting the detectable label conjugated to the biotin analog. The acceptor peptide may have an amino acid sequence comprising SEQ ID NO: 4 or SEQ ID NO: 5, but it is not so limited. In one embodiment, the biotin analog is detected using an antibody. The biotin analog may be detected using a detection system such as but not limited to fluorescent detection system, a luminescent detection system, a photographic film detection system, an enzyme detection system, an electron spin resonance detection system, a scanning tunneling microscopy (STM) detection system, an optical detection system and a nuclear magnetic resonance (NMR) detection system.

In one embodiment, the method further comprises removing unbound biotin analog prior to detecting bound biotin analog. The method may also further comprise identifying a biotin ligase mutant having specificity for a biotin analog and biotin. In a related embodiment, the biotin ligase mutant having specificity for a biotin analog and biotin is identified by contacting biotin with an acceptor peptide in the presence of a candidate molecule, and detecting biotin that is bound to the acceptor peptide, wherein the presence of biotin bound to an acceptor peptide indicates that the candidate molecule is a biotin ligase mutant having specificity for a biotin analog and biotin.

The method may also further comprise isolating the candidate molecule that is a biotin ligase mutant having specificity for a biotin analog or the biotin ligase mutant having specificity for a biotin analog and biotin.

In another aspect, the invention provides a method for identifying a biotin analog having specificity for a biotin ligase mutant comprising combining an acceptor peptide with a labeled biotin in the presence of a biotin ligase mutant and determining a control level of biotin incorporation, combining an acceptor peptide with a labeled biotin and a candidate biotin analog molecule in the presence of a biotin ligase mutant and determining a test level of biotin incorporation, and comparing the control and test levels of biotin incorporation, wherein a test level that is less than a control level is indicative of a biotin analog having specificity for a biotin ligase mutant. Various embodiments relating to the biotin ligase mutant, the biotin analog and the acceptor peptide are recited above.

These and other objects of the invention will be described in further detail in connection with the detailed description of the invention.

BRIEF DESCRIPTION OF THE DRAWINGS

FIG. 7 shows the alignment of the amino acid (SEQ ID NO:1) and nucleotide (SEQ ID NO:2) sequence of wild type biotin ligase.

BRIEF DESCRIPTION OF THE SEQUENCE LISTING

Figure 1A:
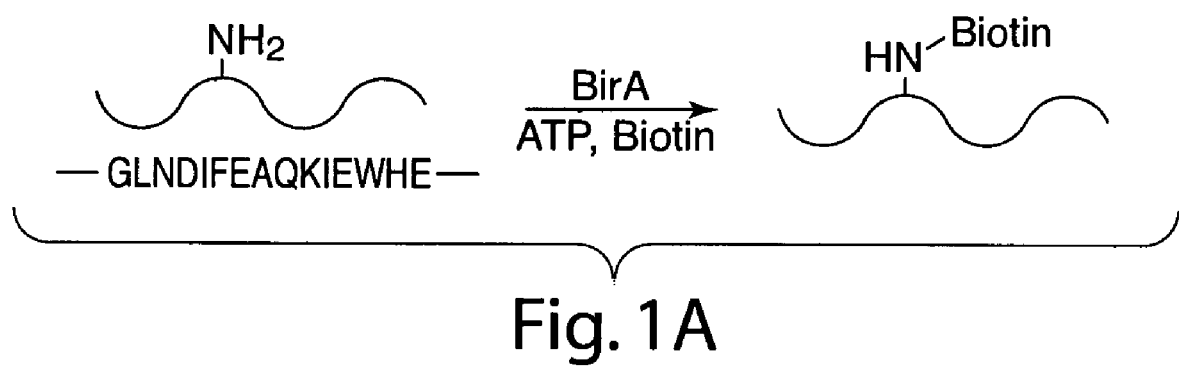
FIG. 1A shows biotinylation of the lysine side chain of the consensus peptide sequence (SEQ ID NO: 5) of biotin ligase (BirA). (Chapman-Smith et al. *J. Nutr.*, 129:477S–484S, 1999).

SEQ ID NO: 1 is the amino acid sequence of wild type biotin ligase.

SEQ ID NO: 2 is the nucleotide sequence of wild type biotin ligase.

SEQ ID NO: 3 is a consensus amino acid sequence of an acceptor peptide.

SEQ ID NO: 4 is the amino acid sequence of a 13 amino acid acceptor peptide.

SEQ ID NO: 5 is the amino acid sequence of an acceptor peptide (AviTag™).

SEQ ID NO: 6 is the amino acid sequence of a biotin ligase mutant having a T90G amino acid substitution.

SEQ ID NO: 7 is the amino acid sequence of a biotin ligase mutant having T90G and N91S amino acid substitutions.

SEQ ID NO: 8 is the amino acid sequence of a biotin ligase mutant having possible amino acid substitutions at amino acid positions 83, 89, 90, 91, 92, 107, 112, 115, 116, 117, 118, 123, 132, 134, 142, 186, 188, 189, 190, 204, 206, 207, or 235.

SEQ ID NO: 9 is the amino acid sequence of a biotin ligase mutant having T90G, T90A, or T90V amino acid substitutions.

SEQ ID NO: 10 is the amino acid sequence of a biotin ligase mutant having T90G, T90A, or T90V and N91S, N91G, N91A, or N91L amino acid substitutions.

SEQ ID NO: 11 is the amino acid sequence of a biotin ligase mutant having T90G and N91G amino acid substitutions.

SEQ ID NO: 12 is the amino acid sequence of a biotin ligase mutant having T90A and N91A amino acid substitutions.

SEQ ID NO: 13 is the amino acid sequence of a biotin ligase mutant having T90A and N91L amino acid substitutions.

SEQ ID NO: 14 is the amino acid sequence of a biotin ligase mutant having C107G amino acid substitution.

SEQ ID NO: 15 is the amino acid sequence of a biotin ligase mutant having Q112M amino acid substitution.

SEQ ID NO: 16 is the amino acid sequence of a biotin ligase mutant having G115A amino acid substitution.

SEQ ID NO: 17 is the amino acid sequence of a biotin ligase mutant having Y132G amino acid substitution.

SEQ ID NO: 18 is the amino acid sequence of a biotin ligase mutant having Y132A amino acid substitution.

SEQ ID NO: 19 is the amino acid sequence of a biotin ligase mutant having S134G amino acid substitution.

SEQ ID NO: 20 is the amino acid sequence of a biotin ligase mutant having V189G amino acid substitution.

SEQ ID NO: 21 is the amino acid sequence of a biotin ligase mutant having I207S amino acid substitution.

DETAILED DESCRIPTION OF THE INVENTION

The invention relates to protein labeling in vivo and in vitro. Prior attempts to label specific proteins have been frustrated by a lack of reagents with sufficient specificity. The invention aims to overcome this lack of specificity through the use of biotin ligase mutants and biotin analogs that are recognized by such mutants.

The invention therefore provides, inter alia, methods for labeling proteins in vitro or in vivo. The method generally involves contacting a biotin analog with a fusion protein in the presence of a biotin ligase mutant, and allowing sufficient time for conjugation of the biotin analog to the fusion protein. Times and reaction conditions suitable for biotin ligase mutant activity will generally be comparable to those for wild type biotin ligase which are known in the art. (See for example Examples herein and Avidity technical literature.)

The various components of this reaction will be described in greater detail herein. Briefly, the fusion protein is a fusion of the target protein (i.e., the protein which is to be labeled) and an acceptor peptide (i.e., the peptide sequence that acts as a substrate for the biotin ligase mutant). If the method is performed in vivo, the nucleic acid sequence encoding the fusion protein will be introduced into the cell and transcription and translation allowed to occur. If the method is performed in vitro, the fusion protein will simply be added to the reaction mixture.

As used herein, protein labeling in vitro means labeling of a protein in a cell free environment. As an example, such a protein can be combined with a biotin ligase mutant and a biotin analog under appropriate conditions and thereby labeled, in for example a test tube or a well of a multiwell plate.

As used herein, protein labeling in vivo means labeling of a protein in the context of a cell. The method can be used to label proteins that are intracellular proteins or cell surface proteins. The cell may be present in a subject (e.g., an insect such as Drosophila, a rodent such as a mouse, a human, and the like) or it may be present in culture.

The biotin ligase mutant may also be expressed by the cell in some instances. In other instances, however, the biotin ligase mutant may simply be added to the reaction mixture (if in vitro) or to the cell (if the target protein is a cell surface protein and the acceptor peptide is located on the extracellular domain of the target protein).

According to the method, the biotin ligase mutant conjugates the biotin analog to the acceptor peptide that is fused (either at the nucleic acid level or post-translationally) to the target protein. The method is independent of the protein type and thus any protein can be labeled in this manner. The product of this labeling reaction may or may not be directly detectable however depending upon the nature of the biotin analog, as described herein. Accordingly, it may be necessary to react the conjugated biotin analog with a detectable label. If the method is performed in vivo, the detectable label is preferably one capable of diffusion into a cell. If the method is used to label a cell surface protein, then preferably the biotin analog is labeled with a membrane impermeant label in order to reduce entry and accumulation of the label intracellularly. The biotin analog may be labeled prior to or after conjugation to the fusion protein.

Labeling of proteins allows one to track the movement and activity of such proteins. It also allows cells expressing such proteins to be tracked and imaged, as the case may be. The methods can be used in cells from virtually any organism including insect, yeast, frog, worm, fish, rodent, human and the like.

The method can be used to label virtually any protein. Examples include but are not limited to signal transduction proteins (e.g., cell surface receptors, kinases, adapter proteins), nuclear proteins (transcription factors, histones), mitochondrial proteins (cytochromes, transcription factors) and hormone receptors.

Biotin ligase (BirA) is an 321 amino acid, 33.5 kD enzyme derived from *E. coli* that catalyzes the context-specific conjugation of biotin to a lysine ε-amine in biotin retention and biosynthesis pathways, as shown in FIG. 1A. This reaction is ATP-dependent. As used herein, wild type biotin ligase refers to a naturally occurring bacterial biotin ligase having wild type biotinylation activity. SEQ ID NO: 1 represents the amino acid sequence of wild type biotin ligase (GenBank Accession No. M10123). SEQ ID NO: 2 represents the nucleotide sequence of wild type biotin ligase (GenBank Accession No. M10123).

Biotin ligase is also known as biotin protein ligase, biotin operon repressor protein, BirA, biotin holoenzyme synthetase and biotin-[acetyl-CoA carboxylase] synthetase.

The reaction between biotin ligase and its substrate (discussed below) is referred to as orthogonal. This means that neither the ligase nor its substrate react with any other enzyme or molecule when present either in their native environment (i.e., a bacterial cell) or more importantly for the purposes of the invention in a non-native environment (e.g., a mammalian cell). Accordingly, the invention takes advantage of the high degree of specificity which has evolved between biotin ligase and its substrate.

The only known natural substrate in bacteria of wild type biotin ligase is lysine 122 of the biotin carboxyl carrier protein (BCCP). Chapman-Smith et al. J. Nutr. 129: 477S–484S, 1999.) A 13–15 amino acid minimal substrate sequence encompassing lysine 122 has been identified as the minimal peptide recognition sequence for biotin ligase. As used herein, an "acceptor peptide" is a protein or peptide having an amino acid sequence that is a substrate for a biotin ligase mutant (i.e., a biotin ligase mutant recognizes and is capable of conjugating a biotin analog or biotin to the peptide). The acceptor peptide may have an amino acid sequence of Leu $Xaa_1$ $Xaa_2$ Ile $Xaa_3$ $Xaa_4$ $Xaa_5$ $Xaa_6$ Lys $Xaa_7$ $Xaa_8$ $Xaa_9$ $Xaa_{10}$ (SEQ. ID NO:3), where $Xaa_1$ is any amino acid, $Xaa_2$ is any amino acid other than large hydrophobic amino acids (such as Leu, Val, Ile, Trp, Phe, Tyr); $Xaa_3$ is Phe or Leu, Xaa4 is Glu or Asp; $Xaa_5$ is Ala, Gly, Ser, or Thr; $Xaa_6$ is Gln or Met; $Xaa_7$ is Ile, Met, or Val; $Xaa_8$ is Glu, Leu, Val, Tyr, or Ile; $Xaa_9$ is Trp, Tyr, Val, Phe, Leu, or Ile; and $Xaa_{10}$ is preferably Arg or His but may be any amino acid other than acidic amino acids such as Asp or Glu. Acceptor peptides are known in the art and examples are described in U.S. Pat. Nos. 5,723,584; 5,874,239 and 5,932,433, the entire contents of which are herein incorporated by reference. In important embodiments, the acceptor peptide comprises the amino acid sequence of LNDIFEAQKIEWH (SEQ ID NO: 4). In another embodiment, the acceptor peptide comprises an amino acid sequence of GLN-DIFEAQKIEWHE (SEQ ID NO: 5). Acceptor peptides can be synthesized using standard peptide synthesis techniques. They are also commercially available under the trade name AviTag™ from Avidity (Boulder, Colo.).

The acceptor peptide is used in the methods of the invention to tag target proteins that are to be labeled by biotin ligase mutants. The acceptor peptide and target protein may be fused to each other either at the nucleic acid or amino acid level. Recombinant DNA technology for generating fusion nucleic acids that encode both the target protein and the acceptor peptide are known in the art. Additionally, the acceptor peptide may be fused to the target protein post-translationally. Such linkages may include cleavable linkers or bonds which can be cleaved once the desired labeling is achieved. Such bonds may be cleaved by exposure to a particular pH, or energy of a certain wavelength, and the like. Cleavable linkers are known in the art. Examples include thiol-cleavable cross-linker 3,3'-dithiobis (succinimidyl proprionate), amine-cleavable linkers, and succinyl-glycine spontaneously cleavable linkers.

The acceptor peptide can be fused to the target protein at any position. In some instances, it is preferred that the fusion not interfere with the activity of the target protein, accordingly, the acceptor peptide is fused to the protein at positions that do not interfere with the activity of the protein. Generally, the acceptor peptides can be C- or N-terminally fused to the target proteins. In still other instances, it is possible that the acceptor peptide is fused to the target protein at an internal position (e.g., a flexible internal loop). These proteins are then susceptible to specific tagging by biotin ligase and biotin ligase mutants in vivo and in vitro. This specificity is possible because neither biotin ligase nor the acceptor peptide react with any other enzymes or peptides in a cell.

Thus, the invention is directed in part to generating biotin ligase mutants that recognize biotin analogs and conjugate such analogs to the acceptor peptide. Biotin ligase mutants can be generated in any number of ways, including phage display technology, described in greater detail herein.

The labeling methods of the invention rely on the activity of biotin ligase mutants that recognize and conjugate biotin analogs onto fusion proteins via the acceptor peptide. The invention provides biotin ligase mutants that recognize biotin analogs, and in some instances, biotin itself. As used herein, a biotin ligase mutant is a variant of biotin ligase that is enzymatically active towards a biotin analog (such as those described herein). As used herein, "enzymatically active" means that the mutant is able to recognize and conjugate a biotin analog to the acceptor peptide.

The biotin ligase mutant can have various mutations, including addition, deletion or substitution of one or more amino acids. Preferably, the mutation will be present in the biotin interaction and activation region, spanning amino acids 83–235. Generally, these mutants will possess one or more amino acid substitutions relative to the wild type biotin ligase amino acid sequence (SEQ ID NO:1). In most instances, the biotin ligase mutants do not comprise an amino acid substitution (or other form of mutation) at position 183 (which is the putative catalytic residue) or residues near the peptide binding site and/or the ATP binding site (amino acids 1–26).

Some mutants were developed based on an analysis of the biotin binding site of wild type biotin ligase, particularly in the presence of biotin. Residues that appear important in the interaction with biotin include 89–91, 112, 115–118, 123, 186, 190, 204 and 206. Residues that influence biotin affinity include 83, 107, 115, 118, 142, 189, 207 and 235. Both types of residues are included in the biotin interaction and activation domain. In some important embodiments of the invention, mutants comprise amino acid substitutions at one or more of the following positions: T90, N91, C107, Q112, G115, R116, Y132, S134, L188, V189, I207. Specific examples of biotin ligase mutants are proteins having at least one of the following amino acid substitutions: T90G, T90A, T90V, C107G, Q112M, G115A, Y132A, Y132G, S134G, V189G and I207S. The invention contemplates the use of biotin ligase mutants having an amino acid substitution at one or more of the afore-mentioned positions. Of particular importance are biotin ligase mutants that harbor amino acid substitutions at positions T90 and N91. Examples include but are not limited to T90G/N91S, T90G/N91G, T90A/N91A, T90A/N91 L and T90V/N91L.

The biotin ligase mutant may retain some level of activity for biotin. Its binding affinity for biotin may be similar to that of wild type biotin ligase. Preferably, the mutant has higher binding affinity for a biotin analog than it does for biotin. Consequently, biotin conjugation to an acceptor peptide would be lower in the presence of a biotin analog. In still other embodiments, the biotin ligase mutant has no binding affinity for biotin.

Biotin incorporation can be measured using $^3$H-biotin and measuring incorporation of radioisotope in the peptide. Conjugation of the biotin analog to an acceptor peptide can be assayed based on inhibition of biotin incorporation. In this latter assay, incorporation of a biotin analog is indicated by a reduced amount of incorporated radioactivity since the biotin analog is competed with biotin for conjugation to the acceptor peptide.

The skilled artisan will realize that conservative amino acid substitutions may be made in biotin ligase mutants to provide functionally equivalent variants, i.e., the variants retain the functional capabilities of the particular biotin ligase mutant. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in the amino acid sequence of biotin ligase mutants to produce functionally equivalent variants typically are made by alteration of a nucleic acid encoding the mutant. Such substitutions can be made by a variety of methods known to one of ordinary skill in the art. For example, amino acid substitutions may be made by PCR-directed mutation, site-directed mutagenesis according to the method of Kunkel (Kunkel, PNAS 82: 488–492, 1985), or by chemical synthesis of a nucleic acid molecule encoding a biotin ligase mutant.

Similarly, biotin ligase mutants can be made using standard molecular biology techniques known to those of ordinary skill in the art. For example, the mutants may be formed by transcription and translation from a nucleic acid sequence encoding the mutant. Such nucleic acid sequences can be made based on the teaching of wild type biotin ligase sequence and the position and type of amino acid substitution.

Figure 3A:
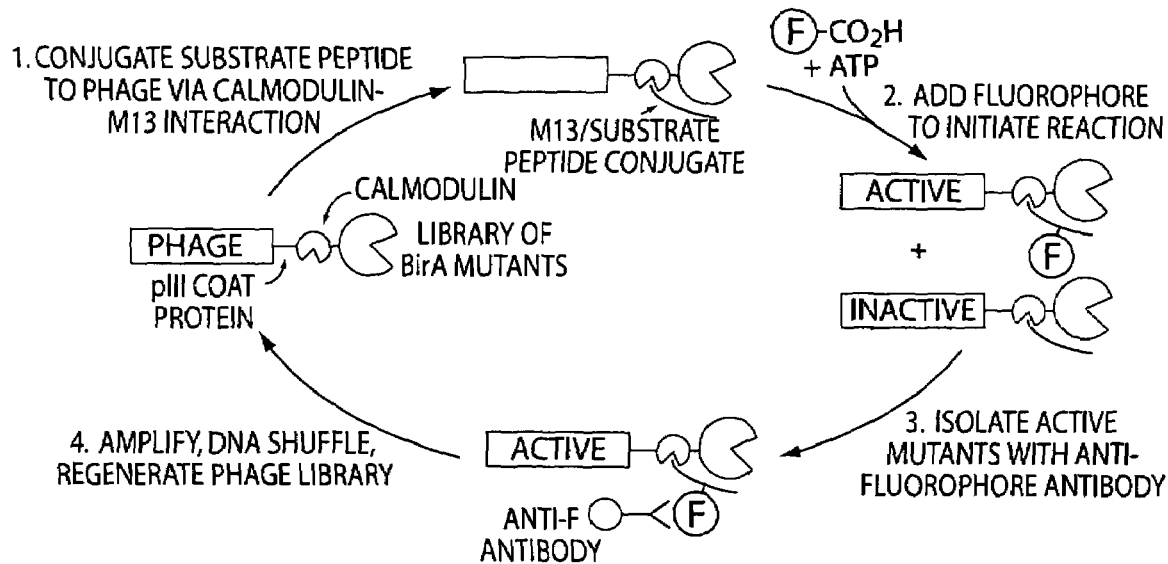
FIG. 3A shows a phage display scheme to select for desired biotin ligase mutants from a library. Wild type biotin ligase has already been successfully displayed on phage and enriched in model selections by Neri et al. (Heinis et al. Protein Engineering 14:1043–1052, 2001.)
Figure 3B:
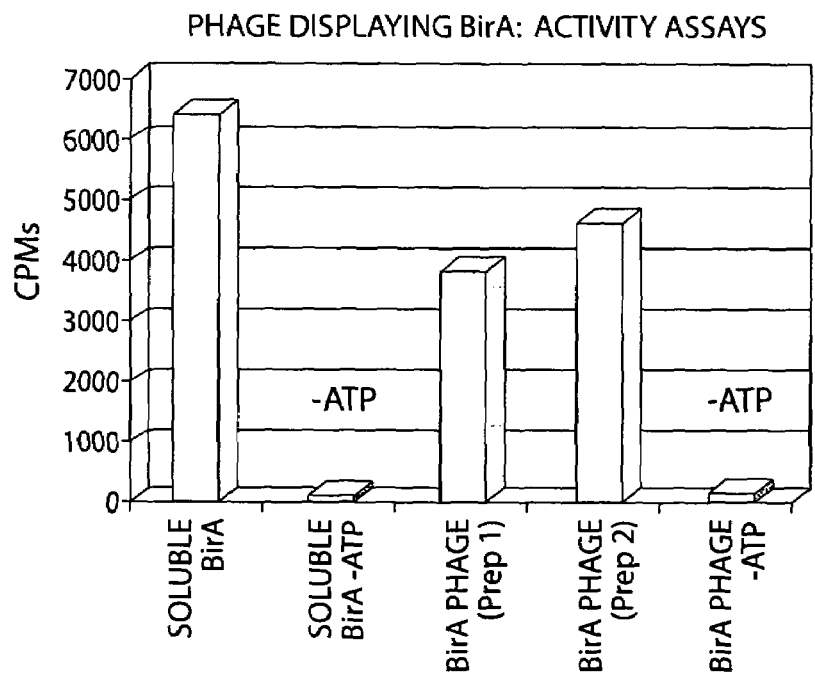
FIG. 3B shows the results of biotinylation activity assays for wild type biotin ligase in soluble or phage displayed form, and either in the presence or absence of ATP.

The invention further provides methods for screening candidate molecules for activity as a biotin ligase mutant. These screening methods can also be combined with methods for generating candidates. One example is a phage display library in which the candidates can be generated and also tested for their ability to conjugate a biotin analog to an acceptor peptide. This is illustrated in FIG. 3 which demonstrates the use of phage having the acceptor peptide present on their coat. Phage that display "active" biotin ligase mutants (i.e., mutants that are able to conjugate a biotin analog (in this case a fluorophore bearing biotin analog) to the acceptor peptide are selected for (using an antibody to the fluorophore). The phage can then optionally be further manipulated to generate derivatives of the active mutant. Phage display library technology is known in the art and has been described extensively. (See for example Benhar, Biotechnol Adv. 2001 Feb. 1;19(1):1–33; Anthony-Cahill et al. Curr Pharm Biotechnol. 2002 December;3(4):299–315, among others.)

Figure 1B:
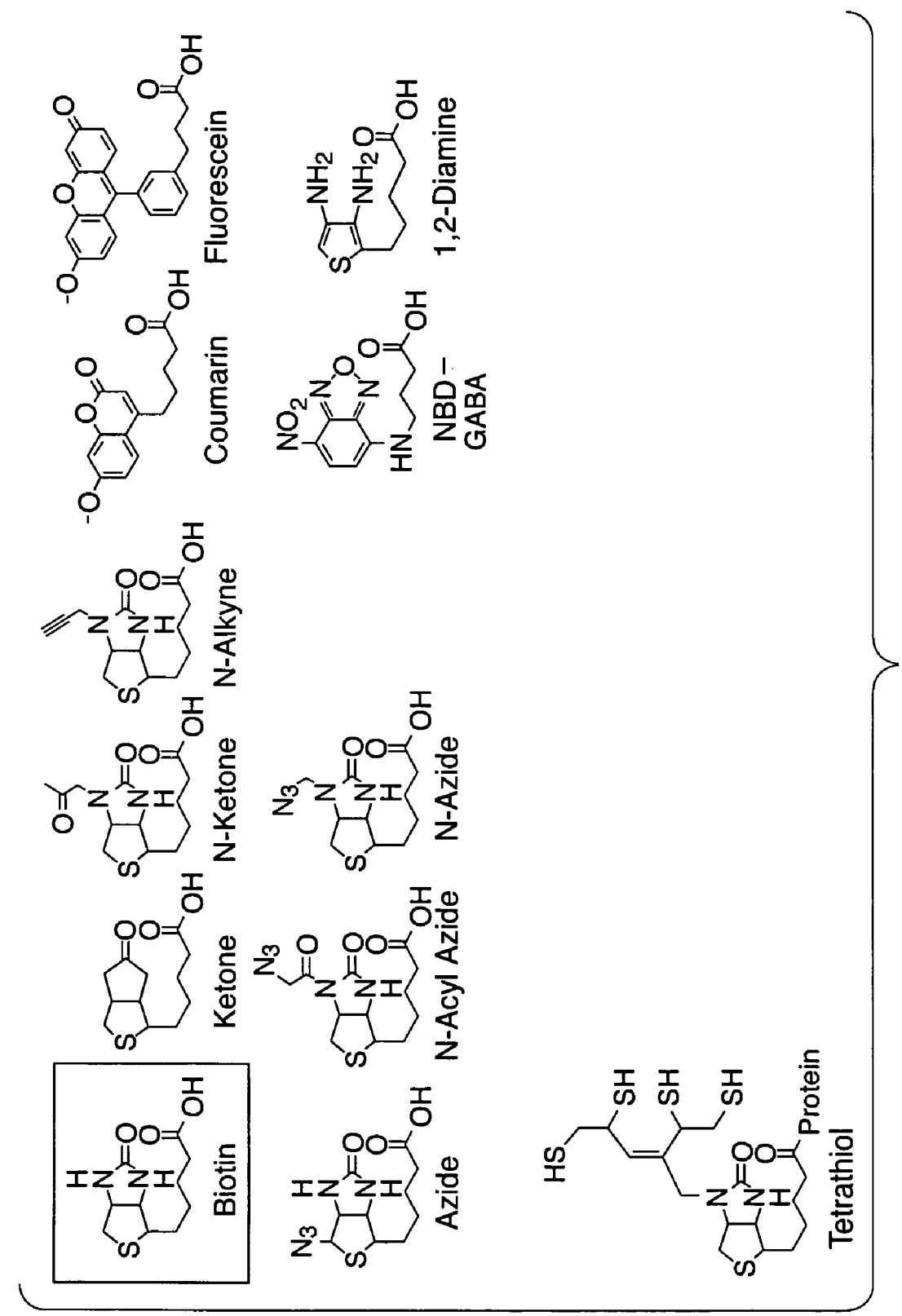
FIG. 1B shows the structures of biotin as well as various biotin analogs. NBD-GABA (7-nitrobenz-2-oxa-1,3-diazole γ-aminobutyric acid) is a fluorophore with a similar size and shape to biotin. Biotin isostere (labeled as ketone) has a bio-orthogonal ketone functionality that can be chemoselectively modified with hydrazine- and alkoxyamine-derivatized probes as shown in FIG. 2. (Cornish et al. *J. Am. Chem. Soc.* 118, 8150–8151, 1996; Mahal et al. *Science* 276, 1125–1128, 1997.) Coumarin and fluorescein are directly detectable biotin analogs.

The labeling methods of the invention further rely on biotin analogs that are recognized and conjugated to acceptor peptides by biotin ligase mutants. As used herein, a biotin analog is a molecule that is structurally similar to biotin. (See for example the structural similarity between ketone biotin analog, azide biotin analog and biotin, as shown in FIG. 1B.) Biotin analogs may share one particular structural feature in common with biotin such as for example an aliphatic carboxylic tail, a two-ring structure, and the like. A biotin analog may be synthesized from biotin, but is not so limited. Examples of biotin analogs of this latter class include biotin methyl ester, desthiobiotin, 2'-iminobiotin, and diaminobiotin. The biotin ligase mutants must be capable of recognizing and conjugating biotin analogs to acceptor peptides, in a manner similar to that in which wild type biotin ligase recognizes and conjugates biotin to the acceptor peptide.

The biotin analog binds to a biotin ligase mutant in the interaction and activation domain. Preferably it binds with an affinity comparable to the binding affinity of wild type biotin ligase to biotin. However, biotin analogs that bind with lower affinities are still useful according to the invention. In some important embodiments, the biotin analog is not recognized by wild type biotin ligase derived from either *E. coli* or from other cell types (e.g., the cell in which the labeling reaction is proceeding).

One category of biotin analogs are molecules having an aliphatic carboxylic acid tail. Examples are shown in FIG. 1B. These include but are not limited to ketone biotin analog, N-ketone biotin analog (e.g., biotin isostere), N-alkyne biotin analog, azide biotin analog, N-acyl azide biotin analog, N-azide biotin analog, coumarin, fluorescein, NBD and 1,2-diamine biotin analog.

Biotin analogs may comprise substitutions (e.g., alkylation) at the trans-ureido nitrogen of biotin. Examples include N-ketone biotin analog, N-alkyne biotin, N-azide and N-acyl azide, all of which are illustrated in FIG. 1B.

Some biotin analogs are not themselves directly detectable, while others are. In the case of the former type, the biotin analog undergoes reaction with another moiety (either before or after conjugation to the acceptor peptide). The subsequent modification of this former type of biotin analog is referred to as a bio-orthogonal ligation reaction and it is used to couple (i.e., label) these biotin analogs to detectable labels such as fluorophores. The resulting moiety may be a hydrazide, phosphine, or azide, but is not so limited. Examples of this former type of biotin analog include ketone biotin analogs, azide biotin analogs, N-acyl azide biotin analogs, N-azide biotin analogs, and tetrathiol biotin analogs, among others. The structures of these biotin analogs are illustrated in FIG. 1B.

Figure 4:
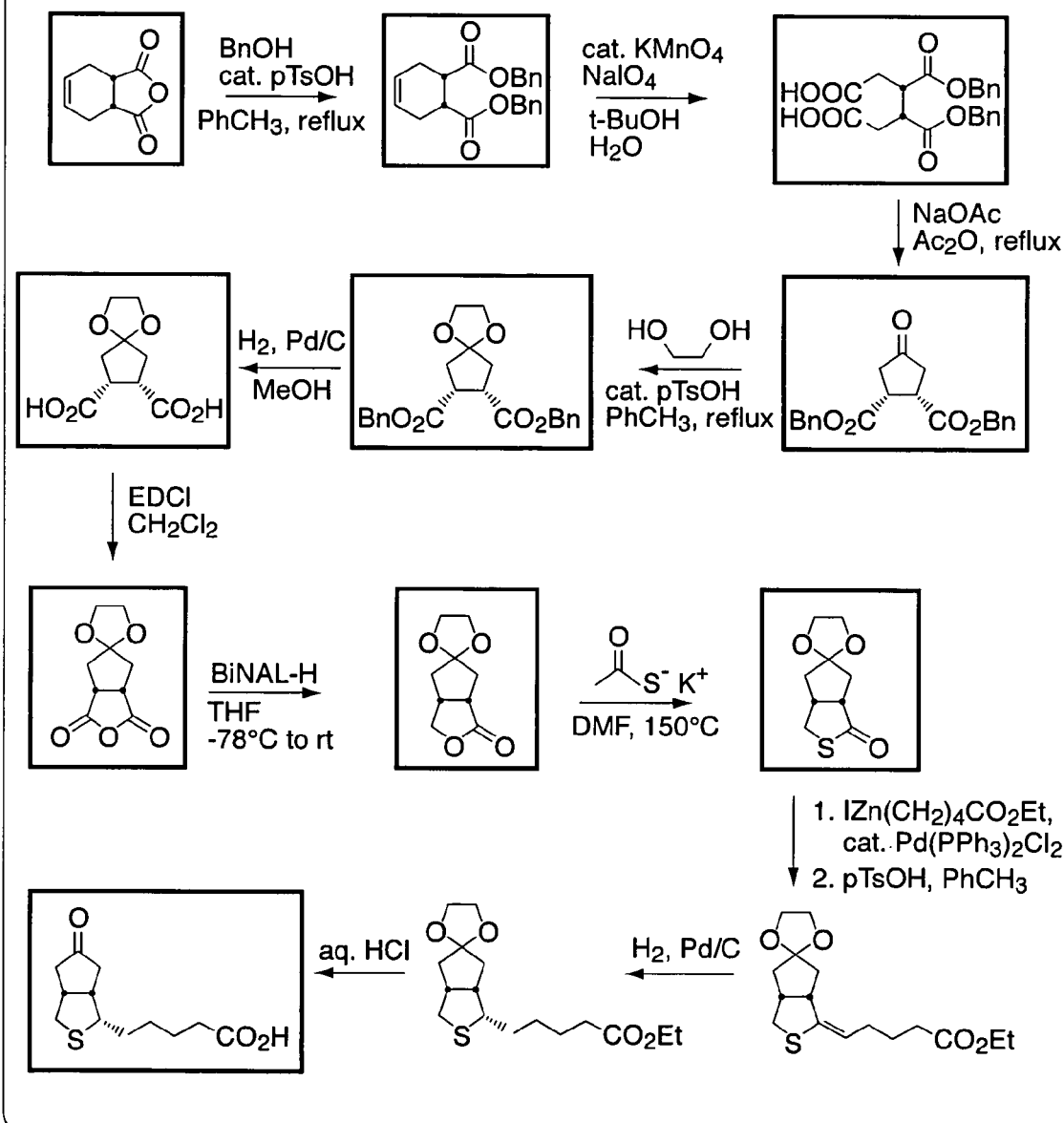
FIG. 4 shows a synthesis pathway for the ketone biotin analog.
Figure 5:
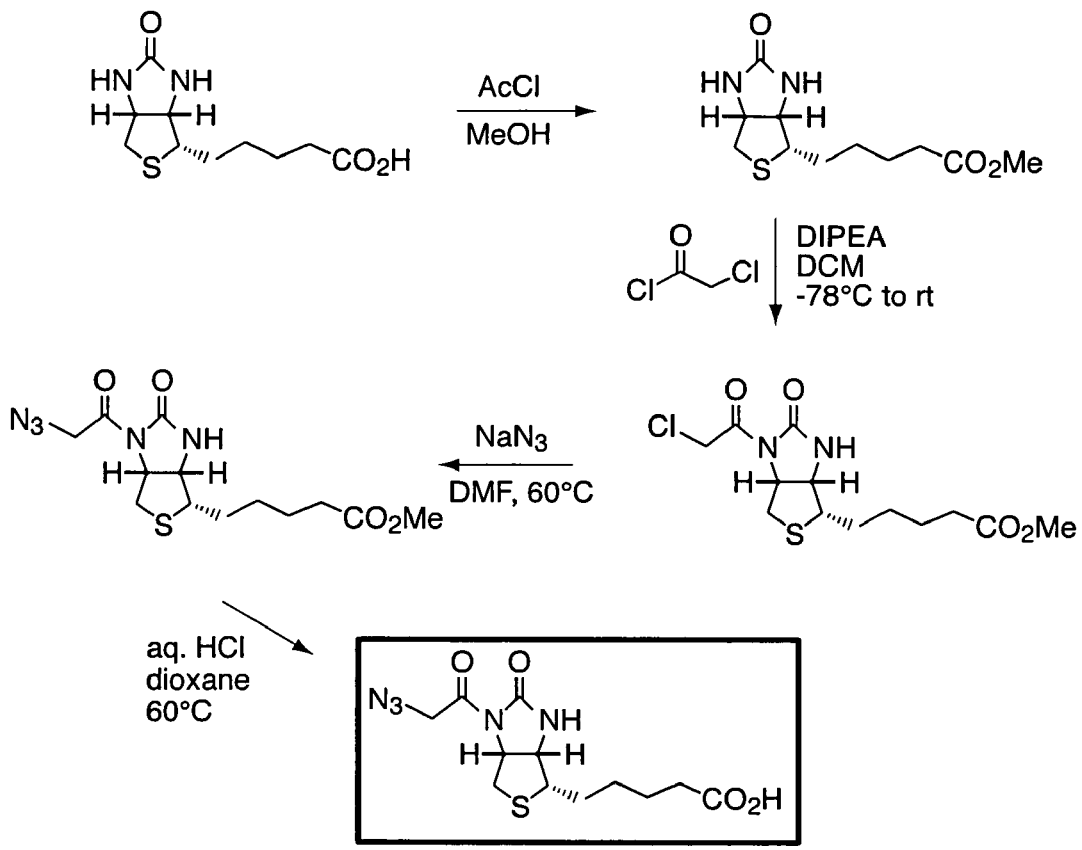
FIG. 5 shows a synthesis pathway for the N-acyl azide and NBD-GABA biotin analogs.
Figure 5:
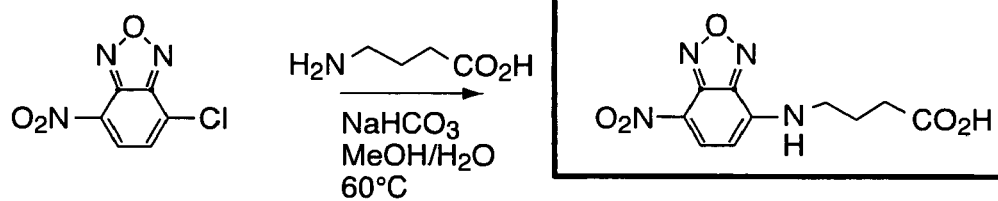
Figure 6A:
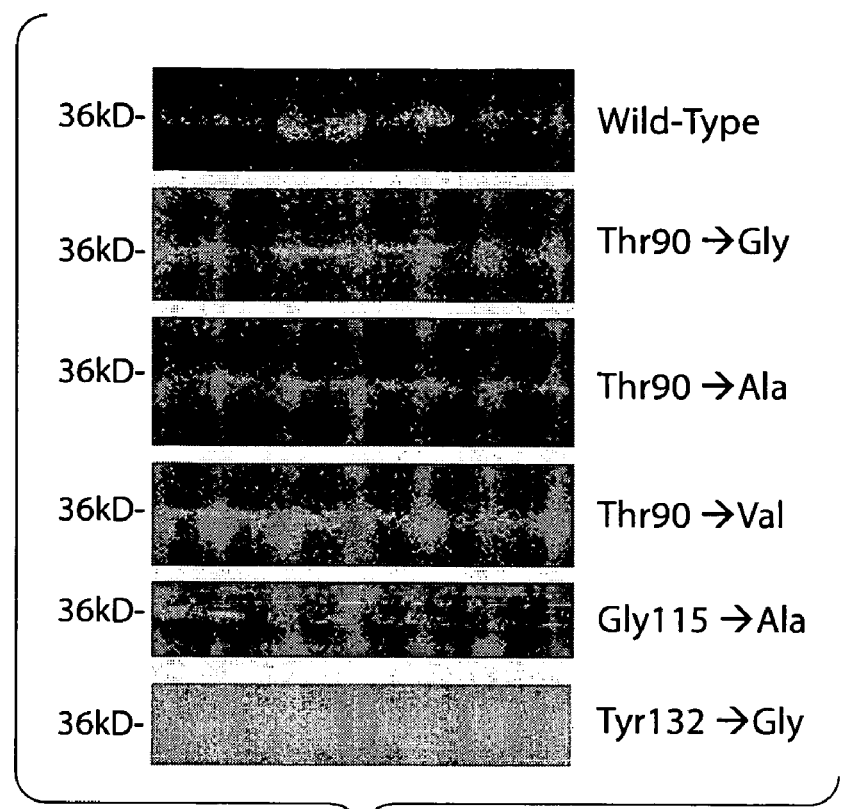
FIG. 6A shows expression of wild type biotin ligase and biotin ligase mutants.
Figure 6B:
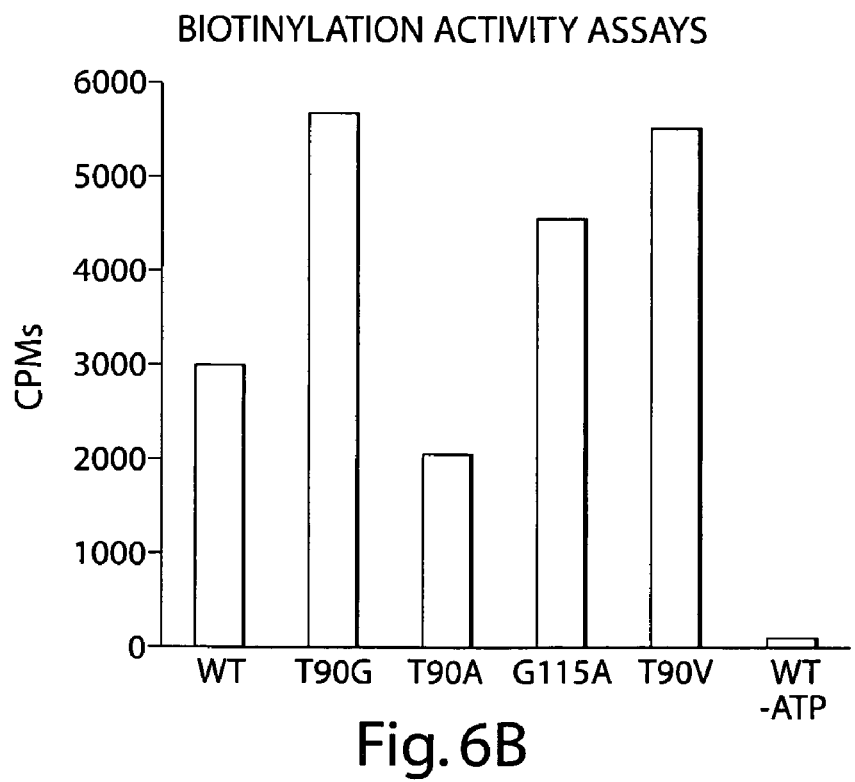
FIG. 6B shows the results of biotinylation activity assays for various biotin ligase mutants. The biotin ligase mutants harboring amino acid substitutions of T90G, G115A or T90V have affinity for biotin comparable to wild type biotin ligase.

FIG. 4 illustrates the synthesis of a ketone biotin analog. FIG. 5 illustrates the synthesis of azide and NBD biotin analogs. These synthesis pathways are exemplary and other synthesis protocols can be used to generate these biotin analogs.

Figure 2:
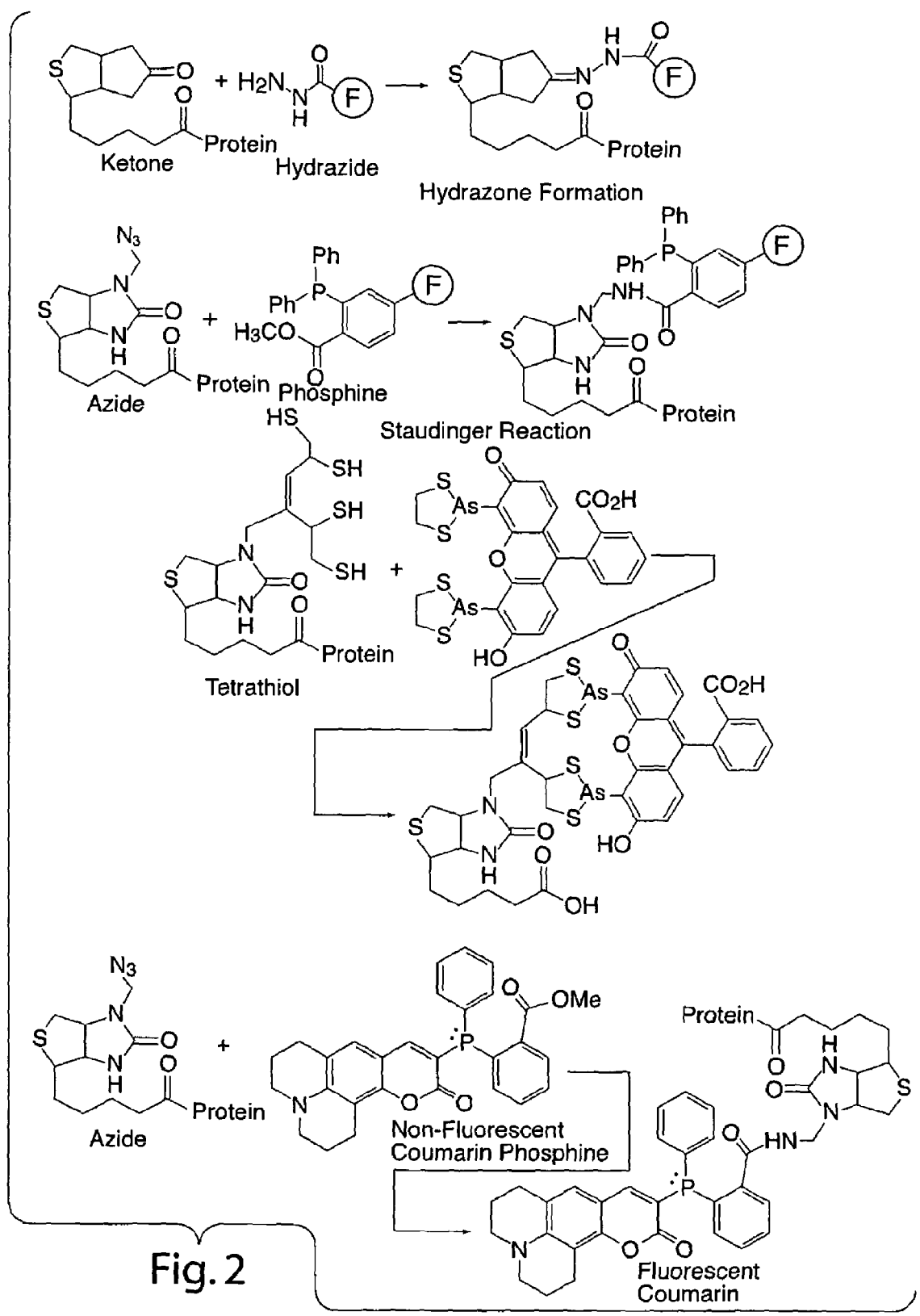
FIG. 2 shows the labeling of biotin analogs with labels. Biotin analogs that introduce unique chemical handles for subsequent modification by a range of probes in the live cell context are shown. "F" represents any fluorophore. The ketone biotin analog can be selectively conjugated to hydrazide, hydroxylamino, and thiosemicarbazide groups under physiological conditions. The azide biotin analog can be selectively coupled to phosphines via the modified Staudinger reaction. (Saxon and Bertozzi, *Science* 287: 2007–2010, 2000.) The tetrathiol biotin analog can form a stable adduct with the fluorescein-arsenic derivative (FlAsH) shown. The reaction of azide with a fluorogenic biotin analog (e.g., non-fluorescent coumarin phosphine) results in a detectable compound (e.g., fluorescent coumarin).

Accordingly, biotin analogs that are not themselves directly detectable must be reacted with a detectable moiety. Each biotin analog in this category will undergo a specific reaction dependent upon its functional groups and that of its reaction partner. Some of these reactions are shown in FIG. 2. The reaction partners in FIG. 2 are fluorophore-bearing, however it is to be understood that the reaction partner may comprise any detectable moiety and is not solely limited to fluorophores. For example, a ketone biotin analog may be reacted with a hydrazine to form a hydrazone. Ketone-hydrazide ligation is fairly rapid and works with high specificity on cell surfaces. (Mahal et al. *Science* 276:1125–1128, 1997.)

In another example, azides may be reacted with phosphines in a Staudinger reaction. Azides and aryl phosphines generally have no cellular counterparts. As a result, the reaction is quite specific. Azide variants with improved stability against hydrolysis in water at pH 6–8 are also useful in the methods of the invention. The alkyne/azide [3+2] cycloaddition chemistry, based on Click chemistry (Wang et al. J. Am. Chem. Soc. 125:11164–11165, 2003), is also specific, in part because the two reactive partners do not have cellular counterparts (i.e., the two functional groups are non-naturally occurring).

As stated above, other biotin analogs may be themselves directly detectable. Examples of such biotin analogs include but are not limited to NBD-GABA, coumarin, fluorescein, Texas Red® (sulforhodamine 101), rhodamine, rosamine, Alexa™ dyes, resorufin, oregon green, tetramethyl rhodamine (TMR), carboxy tetramethyl-rhodamine (TAMRA), Carboxy-X-rhodamine (ROX), BODIPY dyes, and derivatives thereof. Several of these dyes are known in the art and are commercially available (e.g., from Molecular Probes). Several of these molecules are examples of biotin analogs that are not derived from biotin per se. Nonetheless they share structural similarity with biotin, making them suitable biotin analogs for use in the methods of the invention.

The biotin analogs can also be fluorogenic. As used herein, a fluorogenic compound is one that is not detectable (e.g., fluorescent) by itself, but when conjugated to another moiety becomes fluorescent. An example of this is non-fluorescent coumarin phosphine which reacts with azides to produce fluorescent coumarin. Another example of a fluorogenic biotin analog is the diamine biotin analog shown in FIG. 1B. This analog can undergo a condensation with diaminobenzaldehyde to form a fluorescent adduct. (Leandri et al. Gazz. Chim. Ital. 769–839, 1955.) Fluorogenic biotin analogs are especially useful to keeping background to a minimum (e.g., cellular imaging applications).

The invention therefore provides methods for using the afore-mentioned biotin analogs, as well as compositions comprising some of these analogs. For example, the invention provides compositions comprising the NBD-GABA analog, as well as analogs alkyated at the trans-ureido nitrogen group of biotin (e.g., N-ketone biotin analog, ketone biotin analog, N-alkyne biotin analog, N-acyl azide biotin analog and N-azide biotin analog; see FIG. 1B).

As stated above, the biotin analogs can be conjugated to detectable labels. A "detectable label" as used herein is a molecule or compound that can be detected by a variety of methods including fluorescence, electrical conductivity, radioactivity, size, and the like. The label may be of a chemical (e.g., carbohydrate, lipid, etc.), peptide or nucleic acid nature although it is not so limited. The label may be directly or indirectly detectable. The label can be detected directly for example by its ability to emit and/or absorb light of a particular wavelength. A label can be detected indirectly by its ability to bind, recruit and, in some cases, cleave (or be cleaved by) another compound, thereby emitting or absorbing energy. An example of indirect detection is the use of an enzyme label which cleaves a substrate into visible products.

The type of label used will depend on a variety of factors, such as but not limited to the nature of the protein ultimately being labeled. The label should be sterically and chemically compatible with the biotin analog, the acceptor peptide and the target protein. In most instances, the label should not interfere with the activity of the target protein.

Generally, the label can be selected from the group consisting of a fluorescent molecule, a chemiluminescent molecule (e.g., chemiluminescent substrates), a phosphorescent molecule, a radioisotope, an enzyme, an enzyme substrate, an affinity molecule, a ligand, an antigen, a hapten, an antibody, an antibody fragment, a chromogenic substrate, a contrast agent, an MRI contrast agent, a PET label, a phosphorescent label, and the like.

Specific examples of labels include radioactive isotopes such as $^{32}P$ or $^{3}H$; haptens such as digoxigenin and dintrophenyl; affinity tags such as a FLAG tag, an HA tag, a histidine tag, a GST tag; enzyme tags such as alkaline phosphatase, horseradish peroxidase, beta-galactosidase, etc. Other labels include fluorophores such as fluorescein isothiocyanate ("FITC"), Texas Red®, tetramethylrhodamine isothiocyanate ("TRITC"), 4, 4-difluoro-4-bora-3a, and 4a-diaza-s-indacene ("BODIPY"), Cy-3, Cy-5, Cy-7, Cy-Chrome™, R-phycoerythrin (R-PE), PerCP, allophycocyanin (APC), PharRed™, Mauna Blue, Alexa™ 350 and other Alexa™ dyes, and Cascade Blue®.

The labels can also be antibodies or antibody fragments or their corresponding antigen, epitope or hapten binding partners. Detection of such bound antibodies and proteins or peptides is accomplished by techniques well known to those skilled in the art. Antibody/antigen complexes which form in response to hapten conjugates are easily detected by linking a label to the hapten or to antibodies which recognize the hapten and then observing the site of the label. Alternatively, the antibodies can be visualized using secondary antibodies or fragments thereof that are specific for the primary antibody used. Polyclonal and monoclonal antibodies may be used. Antibody fragments include Fab, F(ab)$_2$, Fd and antibody fragments which include a CDR3 region. The conjugates can also be labeled using dual specificity antibodies.

The label can be a contrast agent. Contrast agents are molecules that are administered to a subject to enhance a particular imaging modality such as but not limited to X-ray, ultrasound, and MRI. Examples of contrast agents for transesophageal echocardiography (TEE) and transcranial Doppler sonography: Echovist((R))-300 ( (TCD)); for MRI: superparamagnetic vascular contrast agent (MION), gadolinium(III), Gd-DTPA-BMA, superparamagnetic iron oxide (SPIO) SH U 555 A, gadoxetic acid; for ultrasonographic (US) angiography: microbubble-based US contrast agent (FS069); for computed tomography: iopamidol; for X-ray venography: NC100150.

The label can be a positron emission tomography (PET) label such as 99 m technetium and 18FDG.

The label can also be an singlet oxygen radical generator including but not limited to resorufin, malachite green, fluorescein, benzidine and its analogs including 2-aminobiphenyl, 4-aminobiphenyl, 3,3'-diaminobenzidine, 3,3'-dichlorobenzidine, 3,3'-dimethoxybenzidine, and 3,3'-dimethylbenzidine. These molecules are useful in EM staining and can also be used to induce localized toxicity.

The label can also be an analyte-binding group such as but not limited to a metal chelator (e.g., a copper chelator). Examples of metal chelators include EDTA, EGTA, and molecules having pyridinium substituents, imidazole substituents, and/or thiol substituents. These labels can be used to analyze local environment of the target protein (e.g., $Ca^{2+}$ concentration).

The label can also be a heavy atom carrier. Such labels would be particularly useful for X-ray crystallographic study of the target protein. Heavy atoms used in X-ray crystallography include but are not limited to Au, Pt and Hg. An example of a heavy atom carrier is iodine.

The label may also be a photoactivatable cross-linker. A photoactivable cross linker is a cross linker that becomes reactive following exposure to radiation (e.g., a ultraviolet radiation, visible light, etc.). Examples include benzophenones, aziridines, a photoprobe analog of geranylgeranyl diphosphate (2-diazo-3,3,3-trifluoropropionyloxy-farnesyl diphosphate or DATFP-FPP) (Quellhorst et al. J Biol Chem. 2001 Nov. 2;276(44):40727–33), a DNA analogue 5-[N-(p-azidobenzoyl)-3-aminoallyl]-dUTP (N(3)RdUTP), sulfosuccinimidyl-2(7-azido-4-methylcoumarin-3-acetamido)-ethyl-1,3'- dithiopropionate (SAED) and 1-[N-(2-hydroxy-5-azidobenzoyl)-2-aminoethyl]-4-(N-hydroxysuccinimidyl)-succinate.

The label may also be a photoswitch label. A photoswitch label is a molecule that undergoes a conformational change in response to radiation. For example, the molecule may change its conformation from cis to trans and back again in response to radiation. The wavelength required to induce the conformational switch will depend upon the particular photoswitch label. Examples of photoswitch labels include azobenzene, 3-nitro-2-naphthalenemethanol. Examples of photoswitches are also described in van Delden et al. Chemistry. 2004 Jan. 5;10(1):61–70; van Delden et al. Chemistry. 2003 Jun. 16;9(12):2845–53; Zhang et al. Bioconjug Chem. 2003 July–August;14(4):824–9; Irie et al. Nature. 2002 Dec. 19–26;420(6917):759–60; as well as many others.

The label may also be a photolabile protecting group. Examples of photolabile protecting group include a nitrobenzyl group, a dimethoxy nitrobenzyl group, nitroveratryloxycarbonyl (NVOC), 2-(dimethylamino)-5-nitrophenyl (DANP), Bis(o-nitrophenyl)ethanediol, brominated hydroxyquinoline, and coumarin-4-ylmethyl derivative. Photolabile protecting groups are useful for photocaging reactive functional groups.

The label may comprise non-naturally occurring amino acids. Examples of non-naturally occurring amino acids include for glutamine (Glu) or glutamic acid residues: α-aminoadipate molecules; for tyrosine (Tyr) residues: phenylalanine (Phe), 4-carboxymethyl-Phe, pentafluoro phenylalanine (PfPhe), 4-carboxymethyl-L-phenylalanine (cmPhe), 4-carboxydifluoromethyl-L-phenylalanine (F$_2$cmPhe), 4-phosphonomethyl-phenylalanine (Pmp), (difluorophosphonomethyl)phenylalanine (F$_2$Pmp), O-malonyl- L-tyrosine (malTyr or OMT), and fluoro-O-malonyltyrosine (FOMT); for proline residues: 2-azetidinecarboxylic acid or pipecolic acid (which have 6-membered, and 4-membered ring structures respectively); 1-aminocyclohexylcarboxylic acid ($Ac_6c$); 3-(2-hydroxynaphtalen-1-yl)-propyl; S-ethyl-isothiourea; 2-$NH_2$-thiazoline; 2-$NH_2$-thiazole; asparagine residues substituted with 3-indolyl-propyl at the C terminal carboxyl group. Modifications of cysteines, histidines, lysines, arginines, tyrosines, glutamines, asparagines, prolines, and carboxyl groups are known in the art and are described in U.S. Pat. No. 6,037,134. These types of labels can be used to study enzyme structure and function.

The label may be an enzyme or an enzyme substrate. Examples of these include (enzyme (substrate)): Alkaline Phosphatase (4-Methylumbelliferyl phosphate Disodium salt; 3-Phenylumbelliferyl phosphate Hemipyridine salt); Aminopeptidase (L-Alanine-4-methyl-7-coumarinylamide trifluoroacetate; Z-L-arginine-4-methyl-7-coumarinylamide hydrochloride; Z-glycyl-L-proline-4-methyl-7-coumarinylamide); Aminopeptidase B (L-Leucine-4-methyl-7-coumarinylamide hydrochloride); Aminopeptidase M (L-Phenylalanine 4-methyl-7-coumarinylamide trifluoroacetate); Butyrate esterase (4-Methylumbelliferyl butyrate); Cellulase (2-Chloro-4-nitrophenyl-beta-D-cellobioside); Cholinesterase (7-Acetoxy-1-methylquinolinium iodide; Resorufin butyrate); alpha-Chymotrypsin, (Glutaryl-L-phenylalanine 4-methyl-7-coumarinylamide); N-(N-Glutaryl-L-phenylalanyl)-2-aminoacridone; N-(N-Succinyl-L-phenylalanyl)-2-aminoacridone); Cytochrome P450 2B6 (7-Ethoxycoumarin); Cytosolic Aldehyde Dehydrogenase (Esterase Activity) (Resorufin acetate); Dealkylase ($O^7$-Pentylresorufin); Dopamine beta-hydroxylase (Tyramine); Esterase (8-Acetoxypyrene-1,3,6-trisulfonic acid Trisodium salt; 3-(2 Benzoxazolyl)umbelliferyl acetate; 8-Butyryloxypyrene-1,3,6-trisulfonicacid Trisodium salt; 2',7'-Dichrofluorescin diacetate; Fluorescein dibutyrate; Fluorescein dilaurate; 4-Methylumbelliferyl acetate; 4-Methylumbelliferyl butyrate; 8-Octanoyloxypyrene-1,3,6-trisulfonic acid Trisodium salt; 8-Oleoyloxypyrene-1,3,6-trisulfonic acid Trisodium salt; Resorufin acetate); Factor X Activated (Xa) (4-Methylumbelliferyl 4-guanidinobenzoate hydrochloride Monohydrate); Fucosidase, alpha-L-( 4-Methylumbelliferyl-alpha-L-fucopyranoside); Galactosidase, alpha-(4-Methylumbelliferyl-alpha-D galactopyranoside); Galactosidase, beta- (6,8-Difluoro-4-methylumbelliferyl-beta-D-galactopyranoside; Fluorescein di(beta-D-galactopyranoside); 4-Methylumbelliferyl-alpha-D-galactopyranoside; 4-Methylumbelliferyl-beta-D-lactoside: Resorufin-beta-D-galactopyranoside; 4-(Trifluoromethyl) umbelliferyl-beta-D-galactopyranoside; 2-Chloro-4-nitrophenyl-beta-D-lactoside); Glucosaminidase, N-acetyl-beta- (4-Methylumbelliferyl-N-acetyl-beta-D-glucosaminide Dihydrate); Glucosidase, alpha-(4-Methylumbelliferyl-alpha-D-glucopyranoside); Glucosidase, beta- (2-Chloro-4-nitrophenyl-beta-D-glucopyranoside; 6,8-Difluoro-4-methylumbelliferyl-beta-D-glucopyranoside; 4-Methylumbelliferyl-beta-D-glucopyranoside; Resorufin-beta-D-glucopyranoside; 4-(Trifluoromethyl)umbelliferyl-beta-D-glucopyranoside); Glucuronidase, beta-(6,8-Difluoro-4-methylumbelliferyl-beta-D-glucuronide Lithium salt; 4-Methylumbelliferyl-beta-D-glucuronide Trihydrate); Leucine aminopeptidase( L-Leucine-4-methyl-7-coumarinylamide hydrochloride); Lipase (Fluorescein dibutyrate; Fluorescein dilaurate; 4-Methylumbelliferyl butyrate; 4-Methylumbelliferyl enanthate; 4-Methylumbelliferyl oleate; 4-Methylumbelliferyl palmitate; Resorufin butyrate); Lysozyme (4-Methylumbelliferyl-N,N',N'-triacetyl-beta-chitotrioside); Mannosidase, alpha- (4-Methylumbelliferyl-alpha-D-mannopyranoside); Monoamine oxidase (Tyramine); Monooxygenase (7-Ethoxycoumarin); Neuraminidase (4-Methylumbelliferyl-N-acetyl-alpha-D-neuraminic acid Sodium salt Dihydrate); Papain (Z-L-arginine-4-methyl-7-coumarinylamide hydrochloride); Peroxidase (Dihydrorhodamine 123); Phosphodiesterase (1-Naphthyl 4-phenylazophenyl phosphate; 2-Naphthyl 4-phenylazophenyl phosphate); Prolyl endopeptidase (Z-glycyl-L-proline-4-methyl-7-coumarinylamide; Z-glycyl-L-proline-2-naphthylamide; Z-glycyl-L-proline-4-nitroanilide); Sulfatase (4-Methylumbelliferyl sulfate Potassium salt); Thrombin (4-Methylumbelliferyl 4-guanidinobenzoate hydrochloride Monohydrate); Trypsin (Z-L-arginine-4-methyl-7-coumarinylamide hydrochloride; 4-Methylumbelliferyl 4-guanidinobenzoate hydrochloride Monohydrate); Tyramine dehydrogenase (Tyramine).

It is to be understood that many of the foregoing labels can also be biotin analogs. That is, depending upon the particular biotin ligase mutant used, the various aforementioned labels may function as biotin analogs. As such, these biotin analogs would be considered to be directly detectable biotin analogs. In some cases, they would not require further modification.

The labels can be attached to the biotin analogs either before or after the analog has been conjugated to the acceptor peptide, presuming that the label does not interfere with the activity of biotin ligase. Labels can be attached to the biotin analogs by any mechanism known in the art. Some of these mechanisms are already described above for particular analogs. Other examples of functional groups which are reactive with various labels include, but are not limited to, (functional group: reactive group of light emissive compound) activated ester:amines or anilines; acyl azide:amines or anilines; acyl halide:amines, anilines, alcohols or phenols; acyl nitrile:alcohols or phenols; aldehyde:amines or anilines; alkyl halide:amines, anilines, alcohols, phenols or thiols; alkyl sulfonate:thiols, alcohols or phenols; anhydride: alcohols, phenols, amines or anilines; aryl halide:thiols; aziridine:thiols or thioethers; carboxylic acid:amines, anilines, alcohols or alkyl halides; diazoalkane:carboxylic acids; epoxide:thiols; haloacetamide:thiols; halotriazine:amines, anilines or phenols; hydrazine:aldehydes or ketones; hydroxyamine:aldehydes or ketones; imido ester:amines or anilines; isocyanate:amines or anilines; and isothiocyanate: amines or anilines.

The labels are detected using a detection system. The nature of such detection systems will depend upon the nature of the detectable label. The detection system can be selected from any number of detection systems known in the art. These include a fluorescent detection system, a photographic film detection system, a chemiluminescent detection system, an enzyme detection system, an atomic force microscopy (AFM) detection system, a scanning tunneling microscopy (STM) detection system, an optical detection system, a nuclear magnetic resonance (NMR) detection system, a near field detection system, and a total internal reflection (TIR) detection system.

The invention provides in some instances biotin ligase mutants and/or biotin analogs in an isolated form. As used herein, an isolated biotin ligase mutant is a biotin ligase mutant that is separated from its native environment in sufficiently pure form so that it can be manipulated or used for any one of the purposes of the invention. Thus, isolated means sufficiently pure to be used (i) to raise and/or isolate antibodies, (ii) as a reagent in an assay, or (iii) for sequencing, etc.

Isolated biotin analogs similarly are analogs that have been substantially separated from either their native environment (if it exists in nature) or their synthesis environment. Accordingly, the biotin analogs are substantially separated from any or all reagents present in their synthesis reaction that would be toxic or otherwise detrimental to the target protein, the acceptor peptide, the biotin ligase mutant, or the labeling reaction. Isolated biotin analogs, for example, include compositions that comprise less than 25% contamination, less than 20% contamination, less than 15% contamination, less than 10% contamination, less than 5% contamination, or less than 1% contamination (w/w).

The invention further provides nucleic acids coding for biotin ligase mutants. These nucleic acids therefore encode a biotin ligase mutant having an amino acid substitution at one or more of the following residues: 83, 89–91, 107, 112, 115–118, 123, 132, 134, 142, 186, 188, 189, 190, 204, 206, 207 and 235. In some important embodiments, the amino acid substitution is selected from the group consisting of T90G, T90A, T90V, C107G, Q112M, G115A, Y132A, Y132G, S134G, V189G and I207S. Nucleic acids that encode mutants having substitutions at two or more residues, such as T90G/N91S, T90G/N91G, T90A/N91A, T90A/N91 L and T90V/N91L, are also embraced by the invention.

The nucleotide sequence of wild type biotin ligase mutant is provided as SEQ ID NO: 2. One of ordinary skill in the art will be able to determine the codons corresponding to each of the amino acid residues recited herein.

The invention also embraces degenerate nucleic acids that differ from the mutant nucleic acid sequences provided herein in codon sequence due to degeneracy of the genetic code. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating mutant. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences.

The invention also involves expression vectors coding for biotin ligase mutants and host cells containing those expression vectors. Virtually any cells, prokaryotic or eukaryotic, which can be transformed with heterologous DNA or RNA and which can be grown or maintained in culture, may be used in the practice of the invention. Examples include bacterial cells such as E. coli , mammalian cells such as mouse, hamster, pig, goat, primate, etc., and other eukaryotic cells such as Xenopus cells, Drosophila cells, Zebrafish cells, C. elegans cells, and the like. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences (i.e., reporter sequences) suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., beta-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

As used herein, a marker or coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CCAAT sequence, and the like. Especially, such 5' non-transcribed regulatory sequences will include a promoter region which includes a promoter sequence for transcriptional control of the operably joined coding sequence. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous nucleic acid, usually DNA, molecules, encoding a biotin ligase mutant. The heterologous nucleic acid molecules are placed under operable control of transcriptional elements to permit the expression of the heterologous nucleic acid molecules in the host cell.

Preferred systems for mRNA expression in mammalian cells are those such as pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (Nuc. Acids Res. 18:5322, 1990), and its use in transfection experiments is disclosed by, for example, Demoulin (Mol. Cell. Biol. 16:4710–4716, 1996). Still another preferred expression vector is an adenovirus, described by Stratford-Perricaudet, which is defective for E1 and E3 proteins (J. Clin. Invest. 90:626–630, 1992). The use of the adenovirus as an Adeno.P1A recombinant is disclosed by Warnier et al., in intradermal injection in mice for immunization against P1A (Int. J. Cancer, 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

It will also be recognized that the invention embraces the use of the above described, biotin ligase mutant encoding nucleic acid containing expression vectors, to transfect host cells and cell lines, be these prokaryotic (e.g., *E. coli*), or eukaryotic (e.g., rodent cells such as CHO cells, primate cells such as COS cells, Drosophila cells, Zebrafish cells, Xenopus cells, C. elegans cells, yeast expression systems and recombinant baculovirus expression in insect cells). Especially useful are mammalian cells such as human, mouse, hamster, pig, goat, primate, etc., from a wide variety of tissue types including primary cells and established cell lines.

Various methods of the invention also require expression of fusion proteins in vivo. The fusion proteins are generally recombinantly produced proteins that comprise the biotin ligase acceptor peptides. Such fusions can be made from virtually any protein and those of ordinary skill in the art will be familiar with such methods. Further conjugation methodology is also provided in U.S. Pat. Nos. 5,932,433; 5,874,239 and 5,723,584.

In some instances, it may be desirable to place the biotin ligase mutant and possibly the fusion protein under the control of an inducible promoter. An inducible promoter is one that is active in the presence (or absence) of a particular moiety. Accordingly, it is not constitutively active. Examples of inducible promoters are known in the art and include the tetracycline responsive promoters and regulatory sequences such as tetracycline-inducible T7 promoter system, and hypoxia inducible systems (Hu et al. Mol Cell Biol. 2003 December;23(24):9361–74). Other mechanisms for controlling expression from a particular locus include the use of synthetic short interfering RNAs (siRNAs).

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a subject shall mean an organism such as an insect, a yeast cell, a worm, a fish, or a human or animal including but not limited to a dog, cat, horse, cow, pig, sheep, goat, chicken, rodent e.g., rats and mice, primate, e.g., monkey. Subjects include vertebrate and invertebrate species. Subjects can be house pets (e.g., dogs, cats, fish, etc.), agricultural stock animals (e.g., cows, horses, pigs, chickens, etc.), laboratory animals (e.g., mice, rats, rabbits, etc.), zoo animals (e.g., lions, giraffes, etc.), but are not so limited.

The compositions, as described above, are administered in effective amounts for labeling of the target proteins. The effective amount will depend upon the mode of administration, the location of the cells being targeted, the amount of target protein present and the level of labeling desired.

The methods of the invention, generally speaking, may be practiced using any mode of administration that is medically acceptable, meaning any mode that produces effective levels of the active compounds without causing clinically unacceptable adverse effects. A variety of administration routes are available including but not limited to oral, rectal, topical, nasal, intradermal, or parenteral routes. The term "parenteral" includes subcutaneous, intravenous, intramuscular, or infusion.

When peptides are used, in certain embodiments one desirable route of administration is by pulmonary aerosol. Techniques for preparing aerosol delivery systems containing peptides are well known to those of skill in the art. Generally, such systems should utilize components which will not significantly impair the biological properties of the peptides or proteins (see, for example, Sciarra and Cutie, "Aerosols," in *Remington's Pharmaceutical Sciences,* 18th edition, 1990, pp 1694–1712; incorporated by reference). Those of skill in the art can readily determine the various parameters and conditions for producing protein or peptide aerosols without resort to undue experimentation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that subject tolerance permits. Multiple doses per day are contemplated to achieve appropriate systemic levels of compounds.

The agents may be combined, optionally, with a pharmaceutically-acceptable carrier. The term "pharmaceutically-acceptable carrier" as used herein means one or more compatible solid or liquid filler, diluents or encapsulating substances which are suitable for administration into a subject. The term "carrier" denotes an organic or inorganic ingredient, natural or synthetic, with which the active ingredient is combined to facilitate the application. The components of the pharmaceutical compositions also are capable of being commingled with the molecules of the present invention, and with each other, in a manner such that there is no interaction which would substantially impair the desired pharmaceutical efficacy.

The invention in other aspects includes pharmaceutical compositions. When administered, the pharmaceutical preparations of the invention are applied in pharmaceutically-acceptable amounts and in pharmaceutically-acceptably compositions. Such preparations may routinely contain salt, buffering agents, preservatives, compatible carriers, and the like. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

Other delivery systems can include time-release, delayed release or sustained release delivery systems. Such systems can avoid repeated administrations of the labeling reagents. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480.

A preferred delivery system of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2–4.0 μm can encapsulate large macromolecules. RNA, DNA, and intact virions can be encapsulated within the aqueous interior and be delivered to cells in a biologically active form (Fraley, et al., *Trends Biochem. Sci.*, (1981) 6:77). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2, 3 dioleyloxy)-propyl]-N, N, N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, (1985) 3:235–241.

In one important embodiment, the preferred vehicle is a biocompatible microparticle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System"). PCT/US/03307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the fugetactic agents described herein are encapsulated or dispersed within the biocompatible, preferably biodegradable polymeric matrix disclosed in PCT/US/03307.

The polymeric matrix preferably is in the form of a microparticle such as a microsphere (wherein an agent is dispersed throughout a solid polymeric matrix) or a microcapsule (wherein an agent is stored in the core of a polymeric shell). Other forms of the polymeric matrix for containing an agent include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used. Preferably when an aerosol route is used the polymeric matrix and agent are encompassed in a surfactant vehicle. The polymeric matrix composition can be selected.to have both favorable degradation rates and also to be formed of a material which is bioadhesive, to further increase the effectiveness of transfer. The matrix composition also can be selected not to degrade, but rather, to release by diffusion over an extended period of time.

In another important embodiment the delivery system is a biocompatible microsphere that is suitable for local, site-specific delivery. Such microspheres are disclosed in Chickering et al., *Biotech. And Bioeng.*, (1996) 52:96–101 and Mathiowitz et al., *Nature*, (1997) 386:.410–414.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, agents are delivered using a bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butiric acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolyrners and mixtures thereof. In general, these materials degrade either by enzymatic hydrolysis or exposure to water in vivo, by surface or bulk erosion.

Examples of non-biodegradable polymers include ethylene vinyl acetate, poly(meth)acrylic acid, polyamides, copolymers and mixtures thereof.

Bioadhesive polymers of particular interest include bioerodible hydrogels described by H. S. Sawhney, C. P. Pathak and J. A. Hubell in *Macromolecules*, (1993) 26:581–587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In addition, important embodiments of the invention include pump-based hardware delivery systems, some of which are adapted for implantation. Such implantable pumps include controlled-release microchips. A preferred controlled-release microchip is described in Santini, J T Jr., et al., *Nature*, 1999, 397:335–338, the contents of which are expressly incorporated herein by reference.

Use of a long-term sustained release implant may be particularly suitable for treatment of chronic conditions. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The invention will be more fully understood by reference to the following examples. These examples, however, are merely intended to illustrate the embodiments of the invention and are not to be construed to limit the scope of the invention.

EXAMPLES

Introduction

Many natural enzymes have evolved marked substrate specificity to fulfill their biological functions. One examples is *E. coli* enzyme biotin ligase (i.e., BirA) which participates in the transfer of $CO_2$ from bicarbonate to organic acids to form various cellular metabolite. (Chapman-Smith et al. J. Nutr. 129:477S–484S, 1999.) It has only one natural substrate in bacteria: the biotin carboxyl carrier protein (BCCP), which it biotinylates at lysine 122 to prepare it for carboxylation by bicarbonate. Schatz et al. used peptide panning to identify a minimal, 13-amino acid peptide sequence that could be recognized and enzymatically biotinylated by BirA: LNDIFEAQKIEWH (SEQ ID NO:4), where the biotinylated lysine is underlined. (Schatz et al. Biotechnology 11:1138–1143, 1993; Beckett et al. Protein Sci. 8:921–929, 1999.) Purified BirA and cloning vectors for introducing this modification sequence, called "Avi-Tag™," onto proteins of interest for site-specific biotinylation in vitro or in living bacteria are commercially available. (Avidity, Boulder, Colo.) Recently, Strouboulis et al. reported that BirA could also be used to efficiently and specifically biotinylate Avi-tagged proteins in mammalian cells. (de Boer et al. PNAS 100:7480–7485, 2003.) The *E. coli* BirA does not biotinylate any endogenous mammalian proteins, and the mammalian counterpart of BirA does not biotinylate the Avi-Tag.

According to the invention, the biotin binding pocket of BirA was re-engineered to accommodate a range of small-binding site. Two different probes, an N-ketone biotin analog and an N-alkyne biotin analog (FIG. 1B), were found to effectively compete against biotin for binding to two BirA mutants—T90G and T90G/N91S, respectively, as shown in a competitive inhibition assay using $^3$H-labeled biotin (Table 1). The N-ketone and N-alkyne probes both bear substitutions on the trans ureido nitrogen of biotin, which directly interferes with the T90 residue. Reduction of the T90 side chain to a proton (e.g., glycine) makes room for these ketone and alkyne moieties, allowing them to fit into the biotin binding pocket. In the case of the alkyne probe, which has a slightly different geometry than the ketone, additional space generated by changing N91 to serine is required. These results show that the BirA structure is amenable to reengineering and that certain non-naturally occurring biotin analogs (i.e., structurally biotin-like molecules) can be accommodated in the biotin binding site after careful mutagenesis.

TABLE 1

Incorporation of N-ketone and N-alkylene biotin analogsx by the BirA mutants T90G and T90G/N91S, respectively, as measured in a competitive inhibition assay with $^3$H-labeled biotin.

| Mutant | N-Ketone | % Inhibition of $^3$H-biotin incorporation | Mutant | N-Alkylene | % Inhibition of $^3$H-biotin incorporation |
|---|---|---|---|---|---|
| WT | 0 | 0% | WT | 0 | 0% |
| WT | 4 mM | <50% | WT | 2 mM | 5% |
| G115A | 4 mM | <50% | Y132A | 2 mM | 0% |
| T90G/N91S | 4 mM | 80% | G115A | 2 mM | 0% |
| T90V | 4 mM | <50% | Q112M | 2 mM | 1.6% |
| T90A | 4 mM | <50% | T90A | 2 mM | 0% |
| T90G | 4 mM | 100% | T90A/N91A | 2 mM | 0% |
| | | | T90A/N91L | 2 mMN | 0% |
| | | | T90V | 2 mM | 0% |
| | | | T90V/N91L | 2 mM | 1.6% |
| | | | T90G | 2 mM | 12% |
| | | | T90G/N91S | 2 mM | 77% | molecule probes other than biotin. Mutants of BirA that can efficiently catalyze the attachment of various small molecule probes (i.e., biotin analogs) to Avi-tagged protein substrates in vitro and in mammalian cells have been developed. The remaining domains of the protein were left intact, including the residues important for ATP binding, peptide substrate binding, and catalysis. The re-engineered BirA is useful for targeting small molecule detectable (e.g., fluorescent) probes to specific proteins in live cells.

i. Rational Mutation of Biotin Ligase (BirA) Active Site to Relax its Specificity for Biotin.

The published crystallographic and biochemical data were used to design a panel of biotin ligase mutants with altered biotin binding sites. The two co-crystal structures of 33.5 kD BirA complexed to biotin and biotinylated lysine show a binding pocket composed of both hydrophobic residues (186, 204, 206) which contact the thiophene ring of biotin, and hydrophilic residues (89, 90, 112, 115, 116, 118, 123) which form hydrogen bonds to the carbonyl and ureido nitrogen groups. (Wilson et al. PNAS 89:9257–9261, 1992 and Weaver et al. PNAS 98:6045–6050, 2001.) Mutagenesis studies have also identified several "second-shell" amino acids (83, 107, 142, 189, 207) important for biotin affinity.

By inspecting the 2.4 Å BirA-biotin co-crystal structure, several key residues were identified that are directly in contact with the bicyclic core of biotin. These residues were changed individually by mutagenesis to enlarge the biotin Ketones and alkynes are useful functional groups to incorporate into proteins because they can be subsequently ligated in bio-orthogonal conjugation reactions to hydrazide or azide-derivatized fluorophores. For example, specific ketone-hydrazide ligation has been reported by Bertozzi et al. on the surface of live mammalian cells and in cell extracts, and alkyne-azide ligation via a [3+2] cycloaddition reaction has been reported on Cowpea mosaic virus coat proteins and on the surface of bacteria. (Mahal et al. Science 276:1125–1128, 1997; Wang et al. J. Am. Chem. Soc. 125:3192–3193, 2003; Link et al. J. Am. Chem. Soc. 125: 11164–11165, 2003.)

T90G has therefore been identified according to the invention as an important residue for accommodating N-substituted biotin analog type probes. Additional biotin analogs can be tested for incorporation using a panel of seventeen rationally-designed BirA point mutants: T90G, T90V, T90A, T90G/N91S, T90G/N91G, T90A/N91A, T90A/N91L, T90V/N91L, C107G, Q112G, Q112M, G115A, Y132A, Y132G, V189G, S134G, and I207S. Many of the contacts with biotin are via side chains rather than backbone elements, indicating an opportunity to carve out considerable space to accommodate non-naturally occurring probes. Also, there is a large water-filled channel above the ureido moiety of biotin that appears wide enough to accommodate even larger structures (e.g., coumarin and fluorescein).

Mutant BirA can also be expressed, purified and tested in 96-well plates. The western blot assays described herein for analyzing probe incorporation have already been adapted to a plate format for medium throughput.

In addition, amino acids in the biotin binding site are being computationally randomized and subsequently analyzed using particular algorithms to search for protein sequences that bind to various biotin analogs with high affinity.

Biotin analog incorporation can be determined using a variety of assays including but not limited to (1) inhibition of $^3$H-biotin incorporation, (2) western blot detection of unnatural probe conjugation to cyan fluorescent protein (CFP) bearing a C-terminal Avi-Tag, (3) MALDI mass-spectrometric detection of probe attachment to an Avi-Tag peptide substrate, and (4) HPLC. In the first of these assays, biotin analog candidates and biotin are incubated together with the biotin ligase mutant and the acceptor peptide. Decreases in incorporation of radioactivity are indicative of a biotin analog that competes effectively with biotin for the biotin ligase mutant activity. In the second of these assays, biotin analog conjugation to an acceptor peptide is indicated by the use of antibodies specific for the biotin analog or a label conjugated thereto (e.g., an anti-FLAG antibody or an anti-fluorophore antibody). In the third assay, differences in the molecular weight of the acceptor peptide are indicative of incorporation of the biotin analog. In the last of these assay, acceptor peptides with longer retention times are indicative of biotin analog incorporation.

ii. Synthesis of Biotin Analogs with Unique Biophysical or Chemical Properties Such as Fluorescence.

A range of probes for both in vitro and cellular applications was synthesized and tested against the panel of BirA mutants. Synthesis pathways are illustrated in FIGS. 4 and 5. A fluorophore similar in shape and size to the biotin ring system, 7-nitrobenz-2-oxa-1,3-diazole (NBD), has been conjugated to γ-aminobutyric acid (GABA) to yield NBD-GABA biotin analog (FIG. 1B). Initial analysis of NBD-GABA indicates that it has a low fluorescence quantum yield in water and short excitation wavelength (~340 nm), making it suboptimal for live cell imaging. However, its high sensitivity to variations in local environment make it highly useful as an in vitro biophysical probe.

Ketone biotin analog (FIG. 1B) is not by itself a biophysical probe, but once conjugated to a protein of interest, can serve as a chemical handle for selective derivatization with hydrazine or alkoxyamine-bearing probes (FIG. 2). (Cornish et al. J. Am. Chem. Soc. 118:8150–8151, 1996; and Mahal et al. Science 276:1125–1128, 1997.) This chemistry is specific for the introduced ketone over other functionalities present on mammalian cell surfaces. (Mahal et al. Science 276:1125–1128, 1997.) Inside a cell, however, hydrazides must be prevented from coupling to ketone and aldehyde carbonyls of carbohydrates and natural cofactors. This selectivity may be achieved through multivalency (e.g., two modification sequences may be linked in tandem to a protein of interest, and a bis-functionalized fluorophore with two appropriately-spaced hydrazide groups would have a thermodynamic preference for the target protein over endogenous carbonyl compounds). A heterodivalent interaction may also be achieved by introducing a cysteine residue near the lysine modification site in the BirA target sequence and a probe bearing both a hydrazine moiety and a thiol group would be able to form a hydrazone-disulfide macrocyclic adduct.

Two other biotin derivatives that would similarly introduce chemically unique handles for subsequent modification by probes are shown in FIG. 1B. The Staudinger reaction between an azide and a phosphine has been reported in live cells, as has complexation between fluorescein-arsenic and a tetrathiol moiety. (Saxon et al. Science 287:2007–2010, 2000 and Griffin et al. Science 281:269–272, 1998.)

Lastly, probes that provide readouts other than fluorescence, or alter protein function, can also be used with the panel of BirA mutants. Such probes may include MRI contrast reagents, PET labels, phosphorescent or luminescent tags, singlet-oxygen generators for electron microscopy staining, heavy atoms, photoactivatable crosslinkers (e.g., benzophenones), photoswitches (e.g., azobenzenes), and photocaged labels.

iii. Screening of BirA Mutants for Ability to Conjugate Biotin Analogs to a Lysine Side Chain within a 13-Amino Acid Consensus Sequence.

Wild-type BirA and several of the mutants listed herein have been expressed and purified. Screening of these enzymes for ability to conjugate NBD-GABA biotin analog to a cyan fluorescent protein (CFP) substrate with a C-terminal 13-amino acid modification sequence ("CFP- Avi-Tag™") is detected using anti-DNP (dinitrophenyl) antibody (Molecular Probes) in a Western blot format. To detect ketone conjugation, enzymatic reaction mixtures are treated with fluorescein hydrazide, subjected to gel filtration or Ni-NTA purification to separate CFP- AviTag™ (which bears an N-terminal His$_6$ tag) from unreacted dye, and assayed by fluorimetry. Other biotin analogs are screened in a similar manner.

iv. Generation of Further BirA Mutants Using a Phase Library Approach.

Further BirA mutants can be generated using phage display and mammalian cell FACS (fluorescence activated cell sorting). Some of the biotin analogs described herein are sufficiently structurally similar to biotin that they are likely to be accepted by both wild-type BirA or one of the single-point mutants. In some embodiments, wild type BirA may have reduced affinity for the biotin analog however.

For other analogs, more extensive active-site reengineering is required. Instead of screening mutants one-by-one, a more efficient approach uses directed evolution techniques to select suitable BirA mutants from large libraries. Neri et al. have reported the successful display of active wild type BirA on the surface of bacteriophage and developed an in vitro selection scheme for separating active enzymes from inactive ones. (Heinis et al. Protein Engineering, 14:1043–1052, 2001. ) A library of BirA mutants was designed, using the crystal structures and biochemical reports as guides, to be displayed on the surface of bacteriophage. To enrich for suitable BirA mutants, anti-fluorophore antibodies such as anti-DNP or anti-fluorescein as shown in FIG. 3A are used. The BirA library can be DNA-shuffled between selection rounds to increase diversity and hasten consensus towards active BirA mutants. Negative selections against mutants still capable of transferring biotin can also be implemented using streptavidin beads.

A phage display-based selection system for identification of BirA mutants capable of catalyzing biotin analog conjugation to an Avi-Tag peptide has been developed. The selection uses a calmodulin-M13 strategy (Heinis et al. Protein Engineering, 14:1043–1052, 2001) to anchor the Avi-Tag peptide substrate to the protein coat of each phage molecule. The BirA library is joined to calmodulin and this fusion protein is displayed on the phage coat protein pIII. Model selections have demonstrated that phage displaying wild-type BirA can be enriched over phage displaying a dead mutant (G115S) by 42-fold in one round of selection. It has also been shown that phage molecules chemically labeled with the ketone probe or with the NDB probe shown above can be enriched over mock-labeled phage by 14-fold (using antibodies against NBD or the hydrazide-containing epitope ligated to the ketone).

Libraries that are biased for particular mutations are also contemplated. For example, libraries that are based on a T90G amino acid substitution are a starting template for N-substituted biotin analogs. In other instances, the library can be randomized at seven positions near biotin (i.e., 90, 91, 112, 115, 116, 132 and 188). This library has a size of $1.3 \times 10^9$.

Selection in cells is accomplished by co-transfection with a BirA consensus substrate sequence (i.e., the acceptor peptide) fused to cyan fluorescent protein (CFP), which displays fluorescence resonance energy transfer (FRET) to any successfully incorporated probe, allowing FACS selection. The advantage of labeling an already-fluorescent protein is that non-specific labeling of endogenous proteins will not result in a FRET signal. Labeling specificity can be measured using the ratio of FRET to total fluorescence.

v. In Vivo Site-specific Labeling Methodology.

BirA mutants that perform well in vitro are subsequently screened for activity in mammalian cells. First, BirA mutants that specifically label at the target sequence, thereby discriminating against all endogenous mammalian proteins, are selected. E. coli BirA has naturally evolved a significant degree of peptide specificity in its bacterial context. Peptide panning reportedly has shown that the substrate specificities of E. coli BirA and yeast biotin ligase are non-overlapping. (Kiick et al. PNAS 99:19–24, 2000.) To test whether this orthogonality is also found in the desired mammalian intracellular milieu, mammalian cells are transfected with the BirA mutant nucleic acid sequence as described herein and any undesired modification of endogenous mammalian proteins is detected by Western blot. If background labeling is observed, then the peptide substrate specificity of the enzyme will be targeted for re-engineering using the FRET/ total fluorescence ratio readout outlined herein.

Second, biotin analogs must permeate cells and tissues readily. Biotin is too polar to cross the plasma membrane and requires a transporter protein. The methyl ester of biotin, however, crosses membranes readily and is hydrolyzed to biotin intracellularly by endogenous esterases. The membrane permeance of biotin analogs can be tested, using fluorescence as the readout. Probes that are too polar to cross the membrane will be derivatized to their ester form.

Third, mutant BirA expression level must be high enough that target proteins will be labeled efficiently. However, overexpression can lead to toxicity. The selection strategy in some instances would favor a stable cell line that expresses the mutant BirA consistently and at moderate levels. Alternatively, the gene encoding mutant BirA is placed under control of an inducible promoter and enzyme expression is turned on only when needed.

Finally, the unconjugated probe must be washed out in order to minimize background staining (except for fluorogenic compounds such as FlAsH). Repeated washing with fresh growth media may be sufficient in many cases. In others, addition of probe-specific quenching reagents may be helpful for "stickier" small molecules. Examples of probe-specific quenching reagents include ethandithiol (used for example to remove unbound labels in fluorescein arsenic labeling).

vi. Application to the Study of PI3-Kinase Activation Patterns in 3T3-L1 Adipocytes, or Fat Storage Cells, in Response to PDGF (Platelet-derived Growth Factor) and Insulin Stimulation.

As an example, mutant BirA can be applied to the study of PI3-kinase activation in 3T3-L1 adipocytes. These adipocytes display a membrane ruffling response to PDGF and a glucose transport response to insulin, both mediated by PI3-kinase stimulation. These differing downstream effects may result, according to one hypothesis, from activation of spatially and/or temporally separate pools of PI3-kinase. To test this, a two-tag FRET system is constructed by enzymatically labeling the catalytic and regulatory subunits of PI3-kinase inside cells. Small fluorophores should perturb the system far less than fluorescent proteins such as GFP. This system allows measurement of PI3-kinase activation in real time and at subcellular resolution after insulin or PDGF stimulation.

REFERENCES

Keppler, A. et al. A general method for the covalent labeling of fusion proteins with small molecules in vivo. *Nat. Biotechnol.* 21, 86–89 (2003).

Griffin, B. A., Adams, S. R. & Tsien, R. Y. Specific covalent labeling of recombinant protein molecules inside live cells. *Science* 281, 269–272 (1998).

Chapman-Smith, A. & Cronan, J. E., Jr. Molecular biology of biotin attachment to proteins. *J. Nutr.* 129, 477S–484S (1999).

Schatz, P. J. Use of peptide libraries to map the substrate specificity of a peptide-modifying enzyme: a 13 residue consensus peptide specifies biotinylation in *Escherichia coli*. *Biotechnology* (N.Y.) 11, 1138–1143 (1993).

Beckett, D., Kovaleva, E. & Schatz, P. J. A minimal peptide substrate in biotin holoenzyme synthetase-catalyzed biotinylation. *Protein Sci.* 8, 921–929 (1999).

de Boer, E. et al. Efficient biotinylation and single-step purification of tagged transcription factors in mammalian cells and transgenic mice. *Proc. Natl. Acad Sci. U.S.A* 100, 7480–7485 (2003).

Weaver, L. H., Kwon, K., Beckett, D. & Matthews, B. W. Corepressor-induced organization and assembly of the biotin repressor: a model for allosteric activation of a transcriptional regulator. *Proc. Natl. Acad. Sci. U.S.A* 98, 6045–6050 (2001).

Mahal, L. K., Yarema, K. J. & Bertozzi, C. R. Engineering chemical reactivity on cell surfaces through oligosaccharide biosynthesis. *Science* 276, 1125–1128 (1997).

Wang, Q. et al. Bioconjugation by copper(I)-catalyzed azide-alkyne [3+2] cycloaddition. *J. Am. Chem. Soc.* 125, 3192–3193 (2003).

Link, A. J. & Tirrell, D. A. Cell surface labeling of *Escherichia coli* via copper(I)-catalyzed [3+2] cycloaddition. *J. Am. Chem. Soc.* 125, 11164–11165 (2003). Zhang,Z. et al. A new strategy for the site-specific modification of proteins in vivo. *Biochemistry* 42, 6735–6746 (2003).

Kiick, K. L., Saxon, E., Tirrell, D. A. & Bertozzi, C. R. Incorporation of azides into recombinant proteins for chemoselective modification by the Staudinger ligation. *Proc. Nati. Acad. Sci. U. S.A* 99, 19–24 (2002).

Saxon, E. & Bertozzi, C. R. Cell surface engineering by a modified Staudinger reaction. *Science* 287, 2007–2010 (2000).

Leandri, G., Mangini, A., Montanari, F. & Passerini, R. Ricerche sugli eterociclici: spettri di assorbimento U.V. e proprieta cromoforiche. *Gazz. Chim. Ital.* 769–839 (1955).

Looger, L. L., Dwyer, M. A., Smith, J. J. & Hellinga, H. W. Computational design of receptor and sensor proteins with novel functions. *Nature* 423, 185–190 (2003).

Heinis, C. et al. Selection of catalytically active biotin ligase and trypsin mutants by phage display. *Protein Eng* 14, 1043–1052 (2001).

Sato, H., Ikeda, M., Suzuki, K. & Hirayama, K. Site-specific modification of interleukin-2 by the combined use of genetic engineering techniques and transglutaminase. *Biochemistry* 35, 13072–13080 (1996).

Beckett, D., Kovaleva, E. & Schatz, P. J. A minimal peptide substrate in biotin holoenzyme synthetase-catalyzed biotinylation. *Protein Sci.* 8, 921–929 (1999).

Cornish, V. W., Hahn, K. M., Schultz, P. G. Site-Specific Protein Modification Using a Ketone Handle. *J. Am. Chem. Soc.* 118, 8150–8151 (1996).

Wilson, K. P., Shewchuk, L. M., Brennan, R. G., Otsuka, A. J. & Matthews, B. W. *Escherichia coli* biotin holoenzyme synthetase/bio repressor crystal structure delineates the biotin- and DNA-binding domains. *Proc. Natl. Acad. Sci. U.S.A* 89, 9257–9261 (1992).

EQUIVALENTS

It should be understood that the preceding is merely a detailed description of certain embodiments. It therefore should be apparent to those of ordinary skill in the art that various modifications and equivalents can be made without departing from the spirit and scope of the invention, and with no more than routine experimentation. It is intended to encompass all such modifications and equivalents within the scope of the appended claims.

All references, patents and patent applications that are recited in this application are incorporated by reference herein in their entirety.

What is claimed is:

1. A method for labeling a target protein comprising contacting a fusion protein with a biotin analog, and
allowing sufficient time for the biotin analog to be conjugated to the fusion protein via an acceptor peptide, in the presence of a biotin ligase mutant,
wherein the fusion protein is a fusion of the target protein and the acceptor peptide, and
wherein the biotin ligase mutant is a mutant of SEQ ID NO: 1 and comprises one or more amino acid substitutions selected from the group consisting of T90G, T90V, T90A, N91S, C107G, Q112M, G115A, Y132G, Y132A, S134G, V189G and I207S.

2. The method of claim 1, wherein the biotin analog comprises an aliphatic carboxylic acid tail.

3. The method of claim 1, wherein the biotin analog comprises a substitution at a trans-ureido nitrogen (N) of biotin.

4. The method of claim 1, wherein the biotin analog is selected from the group consisting of an N-ketone biotin analog, a ketone biotin analog, an N-azide biotin analog, an azide biotin analog, an N-acyl azide biotin analog, an NBD-GABA biotin analog, a 1,2-diamine biotin analog, an N-alkyne biotin analog and a tetrathiol biotin analog.

5. The method of claim 1, wherein the target protein is a cell surface protein.

6. The method of claim 1, wherein the fusion protein is in a cell.

7. The method of claim 6, wherein the cell expresses the biotin ligase mutant.

8. The method of claim 6, wherein the cell is a eukaryotic cell.

9. The method of claim 6, wherein the cell is a bacterial cell.

10. The method of claim 8, wherein the eukaryotic cell is a mammalian cell, a Drosophila cell, a Zebrafish cell, a Xenopus cell, a yeast cell or a C. elegans cell.

11. The method of claim 1, wherein the acceptor peptide comprises an amino acid sequence of SEQ ID NO: 4.

12. The method of claim 1, wherein the acceptor peptide comprises an amino acid sequence of SEQ ID NO: 5.

13. The method of claim 1, wherein the acceptor peptide is N- or C- terminally fused to the target protein.

14. The method of claim 1, wherein the biotin analog is N-ketone biotin analog.

15. The method of claim 1, wherein the biotin ligase mutant has an amino acid of SEQ ID NO: 6.

16. The method of claim 1, wherein the biotin ligase mutant comprises amino acid substitutions of T90G and N91S.

17. The method of claim 16, wherein the biotin analog is N-alkyne biotin analog.

18. The method of claim 16, wherein the biotin ligase mutant has an amino acid sequence of SEQ ID NO: 7.

19. The method of claim 1, wherein the method is performed in a cell free environment.

20. The method of claim 1, wherein the method is performed in a cell.

21. The method of claim 1, wherein the method is performed in a subject.

22. The method of claim 1, wherein the acceptor peptide is fused to the target protein via a cleavable bond or linker.

* * * * *

UNITED STATES PATENT AND TRADEMARK OFFICE
CERTIFICATE OF CORRECTION

PATENT NO. : 7,172,877 B2  
APPLICATION NO. : 10/754911  
DATED : February 6, 2007  
INVENTOR(S) : Alice Y. Ting Page 1 of 1

It is certified that error appears in the above-identified patent and that said Letters Patent is hereby corrected as shown below:

In Claim 15, column 68, line 39, please delete "amino acid of" and insert --amino acid sequence of--

Signed and Sealed this

Tenth Day of April, 2007

JON W. DUDAS  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,172,877 B2 | Page 1 of 1 |
| APPLICATION NO. | : 10/754911 | |
| DATED | : February 6, 2007 | |
| INVENTOR(S) | : Alice Y. Ting | |

It is certified that error appears in the above-identified patent and that said Letters Patent is hereby corrected as shown below:

In the Specification:

At column 1, line 16-19, please delete the paragraph:

"This invention was made in part with government support under grant number K22-HG002671-01 awarded from the National Institutes of Health. The Government may retain certain rights in the invention."

and insert

-- This invention was made with government support under grant number K22-HG002671 awarded by the National Institutes of Health. The Government has certain rights in this invention. --

Signed and Sealed this
Twenty-second Day of March, 2011

David J. Kappos
*Director of the United States Patent and Trademark Office*

SEQUENCE LISTING

```
<160> NUMBER OF SEQ ID NOS: 21

<210> SEQ ID NO 1
<211> LENGTH: 321
<212> TYPE: PRT
<213> ORGANISM: Escherichia coli Bir A

<400> SEQUENCE: 1

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205
```

```
Met Ala Met Arg Arg Val Glu Glu Ser Val Val Asn Gln Gly Trp Ile
        210                 215                 220
Thr Leu Gln Glu Ala Gly Ile Asn Leu Asp Arg Asn Thr Leu Ala Ala
225                 230                 235                 240
Met Leu Ile Arg Glu Leu Arg Ala Ala Leu Glu Leu Phe Glu Gln Glu
                245                 250                 255
Gly Leu Ala Pro Tyr Leu Ser Arg Trp Glu Lys Leu Asp Asn Phe Ile
                260                 265                 270
Asn Arg Pro Val Lys Leu Ile Ile Gly Asp Lys Glu Ile Phe Gly Ile
            275                 280                 285
Ser Arg Gly Ile Asp Lys Gln Gly Ala Leu Leu Leu Glu Gln Asp Gly
        290                 295                 300
Ile Ile Lys Pro Trp Met Gly Gly Glu Ile Ser Leu Arg Ser Ala Glu
305                 310                 315                 320
Lys
```

<210> SEQ ID NO 2
<211> LENGTH: 966
<212> TYPE: DNA
<213> ORGANISM: Escherichia coli Bir A

<400> SEQUENCE: 2

| | | | | | |
|---|---|---|---|---|---|
| atgaaggata | acaccgtgcc | actgaaattg | attgccctgt | tagcgaacgg | tgaatttcac | 60 |
| tctggcgagc | agttgggtga | aacgctggga | atgagccggg | cggctattaa | taaacacatt | 120 |
| cagacactgc | gtgactgggg | cgttgatgtc | tttaccgttc | cgggtaaagg | atacagcctg | 180 |
| cctgagccta | tccagttact | taatgctaaa | cagatattgg | gtcagctgga | tgcggtagt | 240 |
| gtagccgtgc | tgccagtgat | tgactccacg | aatcagtacc | ttcttgatcg | tatcggagag | 300 |
| cttaaatcgg | gcgatgcttg | cattgcagaa | taccagcagg | ctggccgtgg | tcgccggggt | 360 |
| cggaaatggt | tttcgccttt | tggcgcaaac | ttatatttgt | cgatgttctg | gcgtctggaa | 420 |
| caaggcccgg | cggcggcgat | tggtttaagt | ctggttatcg | gtatcgtgat | ggcggaagta | 480 |
| ttacgcaagc | tgggtgcaga | taaagttcgt | gttaaatggc | taatgaccct | ctatctgcag | 540 |
| gatcgcaagc | tggcaggcat | tctggtggag | ctgactggca | aaactggcga | tgcggcgcaa | 600 |
| atagtcattg | gagccgggat | caacatggca | atgcgccgtg | ttgaagagag | tgtcgttaat | 660 |
| cagggggtgga | tcacgctgca | ggaagcgggg | atcaatctcg | atcgtaatac | gttggcggcc | 720 |
| atgctaatac | gtgaattacg | tgctgcgttg | gaactcttcg | aacaagaagg | attggcacct | 780 |
| tatctgtcgc | gctgggaaaa | gctggataat | tttattaatc | gcccagtgaa | acttatcatt | 840 |
| ggtgataaag | aaatatttgg | catttcacgc | ggaatagaca | aacaggggc | tttattactt | 900 |
| gagcaggatg | gaataataaa | accctggatg | ggcggtgaaa | tatccctgcg | tagtgcagaa | 960 |
| aaataa | | | | | | 966 |

<210> SEQ ID NO 3
<211> LENGTH: 13
<212> TYPE: PRT
<213> ORGANISM: Escherichia coli
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is Asp, Glu, Asn, Gln, Ser, Thr, Gly,
    Ala, Pro, Met or Cys

```
<220> FEATURE:
<221> NAME/KEY: MISC_FEATURE
<222> LOCATION: (5)..(5)
<223> OTHER INFORMATION: Xaa is Phe or Leu
<220> FEATURE:
<221> NAME/KEY: MISC_FEATURE
<222> LOCATION: (6)..(6)
<223> OTHER INFORMATION: Xaa is Glu or Asp
<220> FEATURE:
<221> NAME/KEY: MISC_FEATURE
<222> LOCATION: (7)..(7)
<223> OTHER INFORMATION: Xaa is Ala, Gly, Ser, or Thr
<220> FEATURE:
<221> NAME/KEY: MISC_FEATURE
<222> LOCATION: (8)..(8)
<223> OTHER INFORMATION: Xaa is Gln, or Met
<220> FEATURE:
<221> NAME/KEY: MISC_FEATURE
<222> LOCATION: (10)..(10)
<223> OTHER INFORMATION: Xaa is Ile, Met, or Val
<220> FEATURE:
<221> NAME/KEY: MISC_FEATURE
<222> LOCATION: (11)..(11)
<223> OTHER INFORMATION: Xaa is Glu, Leu, Val, Tyr, or Ile
<220> FEATURE:
<221> NAME/KEY: MISC_FEATURE
<222> LOCATION: (12)..(12)
<223> OTHER INFORMATION: Xaa is Trp, Tyr, Val, Phe, Leu, or Ile
<220> FEATURE:
<221> NAME/KEY: MISC_FEATURE
<222> LOCATION: (13)..(13)
<223> OTHER INFORMATION: Xaa is Asn, Gln, Ser, Thr, Tyr, Gly, Ala,
     Val, Leu, Ile, Pro, Phe, Met, Trp, or Cys

<400> SEQUENCE: 3

Leu Xaa Xaa Ile Xaa Xaa Xaa Xaa Lys Xaa Xaa Xaa Xaa
1               5                   10

<210> SEQ ID NO 4
<211> LENGTH: 13
<212> TYPE: PRT
<213> ORGANISM: Artificial sequence
<220> FEATURE:
<223> OTHER INFORMATION: Oligonucleotide

<400> SEQUENCE: 4

Leu Asn Asp Ile Phe Glu Ala Gln Lys Ile Glu Trp His
1               5                   10

<210> SEQ ID NO 5
<211> LENGTH: 15
<212> TYPE: PRT
<213> ORGANISM: Artificial sequence
<220> FEATURE:
<223> OTHER INFORMATION: Oligonucleotide

<400> SEQUENCE: 5

Gly Leu Asn Asp Ile Phe Glu Ala Gln Lys Ile Glu Trp His Glu
1               5                   10                  15

<210> SEQ ID NO 6
<211> LENGTH: 321
<212> TYPE: PRT
<213> ORGANISM: Escherichia coli

<400> SEQUENCE: 6

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30
```

-continued

```
Arg Ala Ala Ile Asn Lys His Ile Gln Thr Leu Arg Asp Trp Gly Val
            35                  40                  45

Asp Val Phe Thr Val Pro Gly Lys Gly Tyr Ser Leu Pro Glu Pro Ile
        50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Gly Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
290                 295                 300

Ile Ile Lys Pro Trp Met Gly Gly Glu Ile Ser Leu Arg Ser Ala Glu
305                 310                 315                 320

Lys
```

<210> SEQ ID NO 7
<211> LENGTH: 321
<212> TYPE: PRT
<213> ORGANISM: Escherichia coli

<400> SEQUENCE: 7

```
Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80
```

```
Val Ala Val Leu Pro Val Ile Asp Ser Gly Ser Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys

<210> SEQ ID NO 8
<211> LENGTH: 321
<212> TYPE: PRT
<213> ORGANISM: Escherichia coli
<220> FEATURE:
<221> NAME/KEY: MISC_FEATURE
<222> LOCATION: (83)..(83)
<223> OTHER INFORMATION: Xaa is Val, or any other amino acid
<220> FEATURE:
<221> NAME/KEY: MISC_FEATURE
<222> LOCATION: (89)..(89)
<223> OTHER INFORMATION: Xaa is Ser, or any other amino acid
<220> FEATURE:
<221> NAME/KEY: MISC_FEATURE
<222> LOCATION: (90)..(90)
<223> OTHER INFORMATION: Xaa is Thr, or any other amino acid
<220> FEATURE:
<221> NAME/KEY: MISC_FEATURE
<222> LOCATION: (91)..(91)
<223> OTHER INFORMATION: Xaa is Asn, or any other amino acid
<220> FEATURE:
<221> NAME/KEY: MISC_FEATURE
<222> LOCATION: (92)..(92)
<223> OTHER INFORMATION: Xaa is Gln, or any other amino acid
<220> FEATURE:
<221> NAME/KEY: MISC_FEATURE
<222> LOCATION: (107)..(107)
<223> OTHER INFORMATION: Xaa is Cys, or any other amino acid
<220> FEATURE:
<221> NAME/KEY: MISC_FEATURE
<222> LOCATION: (112)..(112)
```

```
<223> OTHER INFORMATION: Xaa is Gln, or any other amino acid
<220> FEATURE:
<221> NAME/KEY: MISC_FEATURE
<222> LOCATION: (115)..(115)
<223> OTHER INFORMATION: Xaa is Gly, or any other amino acid
<220> FEATURE:
<221> NAME/KEY: MISC_FEATURE
<222> LOCATION: (116)..(116)
<223> OTHER INFORMATION: Xaa is Arg, or any other amino acid
<220> FEATURE:
<221> NAME/KEY: MISC_FEATURE
<222> LOCATION: (117)..(117)
<223> OTHER INFORMATION: Xaa is Gly, or any other amino acid
<220> FEATURE:
<221> NAME/KEY: MISC_FEATURE
<222> LOCATION: (118)..(118)
<223> OTHER INFORMATION: Xaa is Arg, or any other amino acid
<220> FEATURE:
<221> NAME/KEY: MISC_FEATURE
<222> LOCATION: (123)..(123)
<223> OTHER INFORMATION: Xaa is Trp, or any other amino acid
<220> FEATURE:
<221> NAME/KEY: MISC_FEATURE
<222> LOCATION: (132)..(132)
<223> OTHER INFORMATION: Xaa is Tyr, or any other amino acid
<220> FEATURE:
<221> NAME/KEY: MISC_FEATURE
<222> LOCATION: (134)..(134)
<223> OTHER INFORMATION: Xaa is Ser, or any other amino acid
<220> FEATURE:
<221> NAME/KEY: MISC_FEATURE
<222> LOCATION: (142)..(142)
<223> OTHER INFORMATION: Xaa is Gly, or any other amino acid
<220> FEATURE:
<221> NAME/KEY: MISC_FEATURE
<222> LOCATION: (186)..(186)
<223> OTHER INFORMATION: Xaa is Gly, or any other amino acid
<220> FEATURE:
<221> NAME/KEY: MISC_FEATURE
<222> LOCATION: (188)..(188)
<223> OTHER INFORMATION: Xaa is Leu, or any other amino acid
<220> FEATURE:
<221> NAME/KEY: MISC_FEATURE
<222> LOCATION: (189)..(189)
<223> OTHER INFORMATION: Xaa is Val, or any other amino acid
<220> FEATURE:
<221> NAME/KEY: MISC_FEATURE
<222> LOCATION: (190)..(190)
<223> OTHER INFORMATION: Xaa is Glu, or any other amino acid
<220> FEATURE:
<221> NAME/KEY: MISC_FEATURE
<222> LOCATION: (204)..(204)
<223> OTHER INFORMATION: Xaa is Gly, or any other amino acid
<220> FEATURE:
<221> NAME/KEY: MISC_FEATURE
<222> LOCATION: (206)..(206)
<223> OTHER INFORMATION: Xaa is Gly, or any other amino acid
<220> FEATURE:
<221> NAME/KEY: MISC_FEATURE
<222> LOCATION: (207)..(207)
<223> OTHER INFORMATION: Xaa is Ile, or any other amino acid
<220> FEATURE:
<221> NAME/KEY: MISC_FEATURE
<222> LOCATION: (235)..(235)
<223> OTHER INFORMATION: Xaa is Arg, or any other amino acid

<400> SEQUENCE: 8

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60
```

-continued

```
Gln Leu Leu Asn Ala Lys Gln Ile Leu Gly Gln Leu Asp Gly Gly Ser
 65                  70                  75                  80

Val Ala Xaa Leu Pro Val Ile Asp Xaa Xaa Xaa Tyr Leu Leu Asp
             85                  90                  95

Arg Ile Gly Glu Leu Lys Ser Gly Asp Ala Xaa Ile Ala Glu Tyr Xaa
                100                 105                 110

Gln Ala Xaa Xaa Xaa Arg Gly Arg Lys Xaa Phe Ser Pro Phe Gly
            115                 120                 125

Ala Asn Leu Xaa Leu Xaa Met Phe Trp Arg Leu Glu Gln Xaa Pro Ala
130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Xaa Ile Xaa Xaa Xaa Leu Thr
            180                 185                 190

Gly Lys Thr Gly Asp Ala Ala Gln Ile Val Ile Xaa Ala Xaa Xaa Asn
        195                 200                 205

Met Ala Met Arg Arg Val Glu Glu Ser Val Val Asn Gln Gly Trp Ile
210                 215                 220

Thr Leu Gln Glu Ala Gly Ile Asn Leu Asp Xaa Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys
```

```
<210> SEQ ID NO 9
<211> LENGTH: 321
<212> TYPE: PRT
<213> ORGANISM: Escherichia coli
<220> FEATURE:
<221> NAME/KEY: MISC_FEATURE
<222> LOCATION: (90)..(90)
<223> OTHER INFORMATION: Xaa is Gly, Ala, or Val

<400> SEQUENCE: 9
```

```
Met Lys Asp Asn Thr Val Pro Leu Lys Leu Ile Ala Leu Leu Ala Asn
  1               5                  10                  15

Gly Glu Phe His Ser Gly Glu Gln Leu Gly Glu Thr Leu Gly Met Ser
                 20                  25                  30

Arg Ala Ala Ile Asn Lys His Ile Gln Thr Leu Arg Asp Trp Gly Val
             35                  40                  45

Asp Val Phe Thr Val Pro Gly Lys Gly Tyr Ser Leu Pro Glu Pro Ile
         50                  55                  60

Gln Leu Leu Asn Ala Lys Gln Ile Leu Gly Leu Asp Gly Gly Ser
 65                  70                  75                  80

Val Ala Val Leu Pro Val Ile Asp Ser Xaa Asn Gln Tyr Leu Leu Asp
```

-continued

```
                85                  90                  95
Arg Ile Gly Glu Leu Lys Ser Gly Asp Ala Cys Ile Ala Glu Tyr Gln
            100                 105                 110
Gln Ala Gly Arg Gly Arg Gly Arg Lys Trp Phe Ser Pro Phe Gly
        115                 120                 125
Ala Asn Leu Tyr Leu Ser Met Phe Trp Arg Leu Glu Gln Gly Pro Ala
    130                 135                 140
Ala Ala Ile Gly Leu Ser Leu Val Ile Gly Ile Val Met Ala Glu Val
145                 150                 155                 160
Leu Arg Lys Leu Gly Ala Asp Lys Val Arg Val Lys Trp Pro Asn Asp
                165                 170                 175
Leu Tyr Leu Gln Asp Arg Lys Leu Ala Gly Ile Leu Val Glu Leu Thr
            180                 185                 190
Gly Lys Thr Gly Asp Ala Ala Gln Ile Val Ile Gly Ala Gly Ile Asn
        195                 200                 205
Met Ala Met Arg Arg Val Glu Glu Ser Val Val Asn Gln Gly Trp Ile
    210                 215                 220
Thr Leu Gln Glu Ala Gly Ile Asn Leu Asp Arg Asn Thr Leu Ala Ala
225                 230                 235                 240
Met Leu Ile Arg Glu Leu Arg Ala Ala Leu Glu Leu Phe Glu Gln Glu
                245                 250                 255
Gly Leu Ala Pro Tyr Leu Ser Arg Trp Glu Lys Leu Asp Asn Phe Ile
            260                 265                 270
Asn Arg Pro Val Lys Leu Ile Ile Gly Asp Lys Glu Ile Phe Gly Ile
        275                 280                 285
Ser Arg Gly Ile Asp Lys Gln Gly Ala Leu Leu Leu Glu Gln Asp Gly
    290                 295                 300
Ile Ile Lys Pro Trp Met Gly Gly Glu Ile Ser Leu Arg Ser Ala Glu
305                 310                 315                 320
Lys

<210> SEQ ID NO 10
<211> LENGTH: 321
<212> TYPE: PRT
<213> ORGANISM: Escherichia coli
<220> FEATURE:
<221> NAME/KEY: MISC_FEATURE
<222> LOCATION: (90)..(90)
<223> OTHER INFORMATION: Xaa is Gly, Ala, or Val
<220> FEATURE:
<221> NAME/KEY: MISC_FEATURE
<222> LOCATION: (91)..(91)
<223> OTHER INFORMATION: Xaa is Ser, Gly, Ala, or Leu

<400> SEQUENCE: 10

Met Lys Asp Asn Thr Val Pro Leu Lys Leu Ile Ala Leu Leu Ala Asn
1               5                   10                  15
Gly Glu Phe His Ser Gly Glu Gln Leu Gly Glu Thr Leu Gly Met Ser
                20                  25                  30
Arg Ala Ala Ile Asn Lys His Ile Gln Thr Leu Arg Asp Trp Gly Val
            35                  40                  45
Asp Val Phe Thr Val Pro Gly Lys Gly Tyr Ser Leu Pro Glu Pro Ile
        50                  55                  60
Gln Leu Leu Asn Ala Lys Gln Ile Leu Gly Gln Leu Asp Gly Gly Ser
65                  70                  75                  80
Val Ala Val Leu Pro Val Ile Asp Ser Xaa Xaa Gln Tyr Leu Leu Asp
                85                  90                  95
```

-continued

Arg Ile Gly Glu Leu Lys Ser Gly Asp Ala Cys Ile Ala Glu Tyr Gln
            100                 105                 110

Gln Ala Gly Arg Gly Arg Gly Arg Lys Trp Phe Ser Pro Phe Gly
        115                 120                 125

Ala Asn Leu Tyr Leu Ser Met Phe Trp Arg Leu Glu Gln Gly Pro Ala
        130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
        210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
        290                 295                 300

Ile Ile Lys Pro Trp Met Gly Gly Glu Ile Ser Leu Arg Ser Ala Glu
305                 310                 315                 320

Lys

<210> SEQ ID NO 11
<211> LENGTH: 321
<212> TYPE: PRT
<213> ORGANISM: Escherichia coli

<400> SEQUENCE: 11

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Gly Gly Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
        130                 135                 140

```
Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
            165                 170                 175

Leu Tyr Leu Gln Asp Arg Lys Leu Ala Gly Ile Leu Val Glu Leu Thr
                180                 185                 190

Gly Lys Thr Gly Asp Ala Ala Gln Ile Val Ile Gly Ala Gly Ile Asn
            195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
                260                 265                 270

Asn Arg Pro Val Lys Leu Ile Ile Gly Asp Lys Glu Ile Phe Gly Ile
            275                 280                 285

Ser Arg Gly Ile Asp Lys Gln Gly Ala Leu Leu Leu Glu Gln Asp Gly
    290                 295                 300

Ile Ile Lys Pro Trp Met Gly Glu Ile Ser Leu Arg Ser Ala Glu Lys
305                 310                 315                 320

Lys

<210> SEQ ID NO 12
<211> LENGTH: 321
<212> TYPE: PRT
<213> ORGANISM: Escherichia coli

<400> SEQUENCE: 12

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Ala Ala Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190
```

-continued

```
Gly Lys Thr Gly Asp Ala Ala Gln Ile Val Ile Gly Ala Gly Ile Asn
            195                 200                 205

Met Ala Met Arg Arg Val Glu Glu Ser Val Val Asn Gln Gly Trp Ile
        210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys
```

<210> SEQ ID NO 13
<211> LENGTH: 321
<212> TYPE: PRT
<213> ORGANISM: Escherichia coli

<400> SEQUENCE: 13

```
Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Ala Leu Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240
```

```
Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Glu Gln Asp Gly
    290                 295                 300

Ile Ile Lys Pro Trp Met Gly Glu Ile Ser Leu Arg Ser Ala Glu
305                 310                 315                 320

Lys

<210> SEQ ID NO 14
<211> LENGTH: 321
<212> TYPE: PRT
<213> ORGANISM: Escherichia coli

<400> SEQUENCE: 14

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Gly Ile Ala Glu Tyr Gln
                100                 105                 110

Gln Ala Gly Arg Gly Arg Arg Gly Arg Lys Trp Phe Ser Pro Phe Gly
            115                 120                 125

Ala Asn Leu Tyr Leu Ser Met Phe Trp Arg Leu Glu Gln Gly Pro Ala
130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285
```

```
Ser Arg Gly Ile Asp Lys Gln Gly Ala Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys

<210> SEQ ID NO 15
<211> LENGTH: 321
<212> TYPE: PRT
<213> ORGANISM: Escherichia coli

<400> SEQUENCE: 15

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
                20                  25                  30

Arg Ala Ala Ile Asn Lys His Ile Gln Thr Leu Arg Asp Trp Gly Val
            35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Met
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys
```

```
<210> SEQ ID NO 16
<211> LENGTH: 321
<212> TYPE: PRT
<213> ORGANISM: Escherichia coli

<400> SEQUENCE: 16

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Ala Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys

<210> SEQ ID NO 17
<211> LENGTH: 321
<212> TYPE: PRT
<213> ORGANISM: Escherichia coli

<400> SEQUENCE: 17

Met Lys Asp Asn Thr Val Pro Leu Lys Leu Ile Ala Leu Leu Ala Asn
```

```
              1               5                  10                 15
Gly Glu Phe His Ser Gly Glu Gln Leu Gly Glu Thr Leu Gly Met Ser
                20                  25                 30

Arg Ala Ala Ile Asn Lys His Ile Gln Thr Leu Arg Asp Trp Gly Val
                35                  40                 45

Asp Val Phe Thr Val Pro Gly Lys Gly Tyr Ser Leu Pro Glu Pro Ile
                50                  55                 60

Gln Leu Leu Asn Ala Lys Gln Ile Leu Gly Gln Leu Asp Gly Gly Ser
65                  70                  75                 80

Val Ala Val Leu Pro Val Ile Asp Ser Thr Asn Gln Tyr Leu Leu Asp
                85                  90                 95

Arg Ile Gly Glu Leu Lys Ser Gly Asp Ala Cys Ile Ala Glu Tyr Gln
                100                 105                110

Gln Ala Gly Arg Gly Arg Arg Gly Arg Lys Trp Phe Ser Pro Phe Gly
                115                 120                125

Ala Asn Leu Gly Leu Ser Met Phe Trp Arg Leu Glu Gln Gly Pro Ala
                130                 135                140

Ala Ala Ile Gly Leu Ser Leu Val Ile Gly Ile Val Met Ala Glu Val
145                 150                 155                160

Leu Arg Lys Leu Gly Ala Asp Lys Val Arg Val Lys Trp Pro Asn Asp
                165                 170                175

Leu Tyr Leu Gln Asp Arg Lys Leu Ala Gly Ile Leu Val Glu Leu Thr
                180                 185                190

Gly Lys Thr Gly Asp Ala Ala Gln Ile Val Ile Gly Ala Gly Ile Asn
                195                 200                205

Met Ala Met Arg Arg Val Glu Glu Ser Val Val Asn Gln Gly Trp Ile
                210                 215                220

Thr Leu Gln Glu Ala Gly Ile Asn Leu Asp Arg Asn Thr Leu Ala Ala
225                 230                 235                240

Met Leu Ile Arg Glu Leu Arg Ala Ala Leu Glu Leu Phe Glu Gln Glu
                245                 250                255

Gly Leu Ala Pro Tyr Leu Ser Arg Trp Glu Lys Leu Asp Asn Phe Ile
                260                 265                270

Asn Arg Pro Val Lys Leu Ile Ile Gly Asp Lys Glu Ile Phe Gly Ile
                275                 280                285

Ser Arg Gly Ile Asp Lys Gln Gly Ala Leu Leu Leu Glu Gln Asp Gly
                290                 295                300

Ile Ile Lys Pro Trp Met Gly Gly Glu Ile Ser Leu Arg Ser Ala Glu
305                 310                 315                320

Lys

<210> SEQ ID NO 18
<211> LENGTH: 321
<212> TYPE: PRT
<213> ORGANISM: Escherichia coli

<400> SEQUENCE: 18

Met Lys Asp Asn Thr Val Pro Leu Lys Leu Ile Ala Leu Leu Ala Asn
1               5                   10                 15

Gly Glu Phe His Ser Gly Glu Gln Leu Gly Glu Thr Leu Gly Met Ser
                20                  25                 30

Arg Ala Ala Ile Asn Lys His Ile Gln Thr Leu Arg Asp Trp Gly Val
                35                  40                 45

Asp Val Phe Thr Val Pro Gly Lys Gly Tyr Ser Leu Pro Glu Pro Ile
```

-continued

```
                    50                  55                  60
Gln Leu Leu Asn Ala Lys Gln Ile Leu Gly Gln Leu Asp Gly Gly Ser
 65                  70                  75                  80

Val Ala Val Leu Pro Val Ile Asp Ser Thr Asn Gln Tyr Leu Leu Asp
                     85                  90                  95

Arg Ile Gly Glu Leu Lys Ser Gly Asp Ala Cys Ile Ala Glu Tyr Gln
                100                 105                 110

Gln Ala Gly Arg Gly Arg Gly Arg Lys Trp Phe Ser Pro Phe Gly
                115                 120                 125

Ala Asn Leu Ala Leu Ser Met Phe Trp Arg Leu Glu Gln Gly Pro Ala
130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
                180                 185                 190

Gly Lys Thr Gly Asp Ala Ala Gln Ile Val Ile Gly Ala Gly Ile Asn
                195                 200                 205

Met Ala Met Arg Arg Val Glu Glu Ser Val Val Asn Gln Gly Trp Ile
210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
                260                 265                 270

Asn Arg Pro Val Lys Leu Ile Ile Gly Asp Lys Glu Ile Phe Gly Ile
                275                 280                 285

Ser Arg Gly Ile Asp Lys Gln Gly Ala Leu Leu Leu Glu Gln Asp Gly
                290                 295                 300

Ile Ile Lys Pro Trp Met Gly Gly Glu Ile Ser Leu Arg Ser Ala Glu
305                 310                 315                 320

Lys
```

<210> SEQ ID NO 19
<211> LENGTH: 321
<212> TYPE: PRT
<213> ORGANISM: Escherichia coli

<400> SEQUENCE: 19

```
Met Lys Asp Asn Thr Val Pro Leu Lys Leu Ile Ala Leu Leu Ala Asn
  1               5                  10                  15

Gly Glu Phe His Ser Gly Glu Gln Leu Gly Glu Thr Leu Gly Met Ser
                 20                  25                  30

Arg Ala Ala Ile Asn Lys His Ile Gln Thr Leu Arg Asp Trp Gly Val
                 35                  40                  45

Asp Val Phe Thr Val Pro Gly Lys Gly Tyr Ser Leu Pro Glu Pro Ile
             50                  55                  60

Gln Leu Leu Asn Ala Lys Gln Ile Leu Gly Gln Leu Asp Gly Gly Ser
 65                  70                  75                  80

Val Ala Val Leu Pro Val Ile Asp Ser Thr Asn Gln Tyr Leu Leu Asp
                     85                  90                  95

Arg Ile Gly Glu Leu Lys Ser Gly Asp Ala Cys Ile Ala Glu Tyr Gln
```

-continued

```
                100                 105                 110
Gln Ala Gly Arg Gly Arg Arg Gly Arg Lys Trp Phe Ser Pro Phe Gly
            115                 120                 125
Ala Asn Leu Tyr Leu Gly Met Phe Trp Arg Leu Glu Gln Gly Pro Ala
        130                 135                 140
Ala Ala Ile Gly Leu Ser Leu Val Ile Gly Ile Val Met Ala Glu Val
145                 150                 155                 160
Leu Arg Lys Leu Gly Ala Asp Lys Val Arg Val Lys Trp Pro Asn Asp
                165                 170                 175
Leu Tyr Leu Gln Asp Arg Lys Leu Ala Gly Ile Leu Val Glu Leu Thr
            180                 185                 190
Gly Lys Thr Gly Asp Ala Ala Gln Ile Val Ile Gly Ala Gly Ile Asn
        195                 200                 205
Met Ala Met Arg Arg Val Glu Glu Ser Val Val Asn Gln Gly Trp Ile
    210                 215                 220
Thr Leu Gln Glu Ala Gly Ile Asn Leu Asp Arg Asn Thr Leu Ala Ala
225                 230                 235                 240
Met Leu Ile Arg Glu Leu Arg Ala Ala Leu Glu Leu Phe Glu Gln Glu
                245                 250                 255
Gly Leu Ala Pro Tyr Leu Ser Arg Trp Glu Lys Leu Asp Asn Phe Ile
            260                 265                 270
Asn Arg Pro Val Lys Leu Ile Ile Gly Asp Lys Glu Ile Phe Gly Ile
        275                 280                 285
Ser Arg Gly Ile Asp Lys Gln Gly Ala Leu Leu Leu Glu Gln Asp Gly
    290                 295                 300
Ile Ile Lys Pro Trp Met Gly Gly Glu Ile Ser Leu Arg Ser Ala Glu
305                 310                 315                 320
Lys

<210> SEQ ID NO 20
<211> LENGTH: 321
<212> TYPE: PRT
<213> ORGANISM: Escherichia coli

<400> SEQUENCE: 20

Met Lys Asp Asn Thr Val Pro Leu Lys Leu Ile Ala Leu Leu Ala Asn
1               5                   10                  15
Gly Glu Phe His Ser Gly Glu Gln Leu Gly Glu Thr Leu Gly Met Ser
            20                  25                  30
Arg Ala Ala Ile Asn Lys His Ile Gln Thr Leu Arg Asp Trp Gly Val
        35                  40                  45
Asp Val Phe Thr Val Pro Gly Lys Gly Tyr Ser Leu Pro Glu Pro Ile
    50                  55                  60
Gln Leu Leu Asn Ala Lys Gln Ile Leu Gly Gln Leu Asp Gly Gly Ser
65                  70                  75                  80
Val Ala Val Leu Pro Val Ile Asp Ser Thr Asn Gln Tyr Leu Leu Asp
                85                  90                  95
Arg Ile Gly Glu Leu Lys Ser Gly Asp Ala Cys Ile Ala Glu Tyr Gln
            100                 105                 110
Gln Ala Gly Arg Gly Arg Arg Gly Arg Lys Trp Phe Ser Pro Phe Gly
        115                 120                 125
Ala Asn Leu Tyr Leu Ser Met Phe Trp Arg Leu Glu Gln Gly Pro Ala
    130                 135                 140
Ala Ala Ile Gly Leu Ser Leu Val Ile Gly Ile Val Met Ala Glu Val
```

-continued

```
                145                 150                 155                 160
Leu Arg Lys Leu Gly Ala Asp Lys Val Arg Val Lys Trp Pro Asn Asp
                    165                 170                 175

Leu Tyr Leu Gln Asp Arg Lys Leu Ala Gly Ile Leu Gly Glu Leu Thr
                180                 185                 190

Gly Lys Thr Gly Asp Ala Ala Gln Ile Val Ile Gly Ala Gly Ile Asn
                195                 200                 205

Met Ala Met Arg Arg Val Glu Glu Ser Val Val Asn Gln Gly Trp Ile
            210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                    245                 250                 255

Gly Leu Ala Pro Tyr Leu Ser Arg Trp Glu Lys Leu Asp Asn Phe Ile
                260                 265                 270

Asn Arg Pro Val Lys Leu Ile Ile Gly Asp Lys Glu Ile Phe Gly Ile
                275                 280                 285

Ser Arg Gly Ile Asp Lys Gln Gly Ala Leu Leu Leu Glu Gln Asp Gly
            290                 295                 300

Ile Ile Lys Pro Trp Met Gly Glu Ile Ser Leu Arg Ser Ala Glu
305                 310                 315                 320

Lys

<210> SEQ ID NO 21
<211> LENGTH: 321
<212> TYPE: PRT
<213> ORGANISM: Escherichia coli

<400> SEQUENCE: 21

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
                20                  25                  30

Arg Ala Ala Ile Asn Lys His Ile Gln Thr Leu Arg Asp Trp Gly Val
                35                  40                  45

Asp Val Phe Thr Val Pro Gly Lys Gly Tyr Ser Leu Pro Glu Pro Ile
            50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                    85                  90                  95

Arg Ile Gly Glu Leu Lys Ser Gly Asp Ala Cys Ile Ala Glu Tyr Gln
                100                 105                 110

Gln Ala Gly Arg Gly Arg Arg Gly Arg Lys Trp Phe Ser Pro Phe Gly
            115                 120                 125

Ala Asn Leu Tyr Leu Ser Met Phe Trp Arg Leu Glu Gln Gly Pro Ala
        130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                    165                 170                 175

Leu Tyr Leu Gln Asp Arg Lys Leu Ala Gly Ile Leu Val Glu Leu Thr
                180                 185                 190

Gly Lys Thr Gly Asp Ala Ala Gln Ile Val Ile Gly Ala Gly Ser Asn
```

-continued

```
               195                 200                 205
Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
                260                 265                 270

Asn Arg Pro Val Lys Leu Ile Ile Gly Asp Lys Glu Ile Phe Gly Ile
            275                 280                 285

Ser Arg Gly Ile Asp Lys Gln Gly Ala Leu Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys
```